(12) United States Patent
Omary et al.

(10) Patent No.: US 9,872,916 B2
(45) Date of Patent: Jan. 23, 2018

(54) FACILE METHOD FOR MAKING NON-TOXIC BIOMEDICAL COMPOSITIONS COMPRISING HYBRID METAL-POLYMER MICROPARTICLES

(71) Applicant: University of North Texas, Denton, TX (US)

(72) Inventors: Mohammad A. Omary, Denton, TX (US); Sreekar Marpu, Torrance, CA (US)

(73) Assignee: University of North Texas Office of Economic Development and Technology Transfer, Denton, TX (US)

( * ) Notice: Subject to any disclaimer, the term of this patent is extended or adjusted under 35 U.S.C. 154(b) by 0 days.

(21) Appl. No.: 14/390,945

(22) PCT Filed: Apr. 5, 2013

(86) PCT No.: PCT/US2013/035493
§ 371 (c)(1),
(2) Date: Oct. 6, 2014

(87) PCT Pub. No.: WO2013/152314
PCT Pub. Date: Oct. 10, 2013

(65) Prior Publication Data
US 2015/0165056 A1    Jun. 18, 2015

Related U.S. Application Data

(60) Provisional application No. 61/621,148, filed on Apr. 6, 2012.

(51) Int. Cl.
| | |
|---|---|
| A61K 47/48 | (2006.01) |
| A61K 33/38 | (2006.01) |
| G01N 33/50 | (2006.01) |
| G01N 33/536 | (2006.01) |
| A61K 49/00 | (2006.01) |
| B22F 1/00 | (2006.01) |
| A61K 9/50 | (2006.01) |
| B82Y 30/00 | (2011.01) |

(52) U.S. Cl.
CPC ........ *A61K 47/48176* (2013.01); *A61K 9/501* (2013.01); *A61K 9/5026* (2013.01); *A61K 33/38* (2013.01); *A61K 47/4823* (2013.01); *A61K 49/0065* (2013.01); *A61K 49/0091* (2013.01); *B22F 1/0018* (2013.01); *B22F 1/0062* (2013.01); *B82Y 30/00* (2013.01); *G01N 33/5005* (2013.01); *G01N 33/536* (2013.01); *Y10T 436/25* (2015.01)

(58) Field of Classification Search
CPC .............. A61K 47/48176; A61K 33/38; A61K 47/4823; G01N 33/5005; G01N 33/536
USPC .......................... 424/78.26; 435/29; 436/174
See application file for complete search history.

(56) References Cited

U.S. PATENT DOCUMENTS

| | | | |
|---|---|---|---|
| 2008/0241262 A1* | 10/2008 | Lee | A61K 9/0009 424/490 |
| 2009/0281635 A1 | 11/2009 | Li et al. | |
| 2010/0037731 A1 | 2/2010 | Li | |
| 2010/0055199 A1 | 3/2010 | Mansoori | |
| 2010/0056485 A1 | 3/2010 | Park | |
| 2010/0090179 A1 | 4/2010 | Mokhtari | |
| 2010/0172997 A1* | 7/2010 | Omary | A61K 9/5115 424/489 |
| 2011/0193032 A1 | 8/2011 | Shi | |
| 2011/0195131 A1 | 8/2011 | Bouchard et al. | |
| 2011/0200674 A1 | 8/2011 | Mackay | |
| 2011/0204773 A1 | 8/2011 | Yasuda et al. | |
| 2011/0223322 A1 | 9/2011 | Rudhardt et al. | |

FOREIGN PATENT DOCUMENTS

| | | |
|---|---|---|
| WO | 97-47323 A2 | 12/1997 |
| WO | 2011103046 | 8/2001 |
| WO | 01-90226 A1 | 11/2001 |
| WO | 2004089813 | 10/2004 |
| WO | 2008017062 | 2/2008 |
| WO | 2010010122 | 1/2010 |
| WO | 2010048623 A2 | 4/2010 |

OTHER PUBLICATIONS

Bhattarai et al."Hydrophobically modified Chitosan/gold nanoparticles for DNA delivery", J. Nanopart. Res. 2008, 151.
Cho, K. et al. "Thermally responsive poly(N-isopropylacrylamide) monolayer on gold: syntheses, surface characterization, and protein interaction/adsorption studies", Polymer 2004, 45, 3195.
Connor et al., "Gold Nanoparticles are Taken Up by Human Cells but Do Not Cause Acute Cytotoxicity," Small Mar. 2005, 1:3, 325-327.
Das et al. "Microgels loaded with gold nanorods: Photothermally triggered volume phase transition under physiological conditions", Langmuir, 2007, 23, 196.
Dickerson, et al., "Gold nanorod assisted near-infared plasmonic photothermal therapy (PPTT) of squamous cell carcinoma in mice," Cancer Lett. Sep. 28, 2008, 269:1, 57-66.
Dos Santos et al. "Gold nanoparticles embedded, self-sustained Chitosan films as substrates for surface enhanced raman scattering" Langmuir Oct. 16, 2004, 20, (23) 10273-10277.
El-Sayed et al., "Selective laser photo-thermal therapy of epithelial carcinoma using anti-EGFR antibody conjugated gold nanoparticles," Cancer Letters 2006, 239, 129.
Eustis et al., Why gold nanoparticles are more precious than pretty gold: noble metal surface plasmon resonance and its enhancement of the radiative and nonradiative properties . . . Nano Lett. 2005, 5, 829-834.
Guha, S. et al. "Agarose-stabilized gold nanoparticles for surface enhanced Raman spectroscopic detection of DNA nucleosides", Appl. Phys. Lett. 2006, 88, 153114.
Hu et al., "A simple and effective route for the synthesis of crystalline silver nanorods and nanowires," Adv. Func Mat. 2, 14, 183 (2004).

(Continued)

Primary Examiner — Yih-Horng Shiao
(74) Attorney, Agent, or Firm — Edwin S. Flores; Chalker Flores, LLP

(57) ABSTRACT

The present invention includes photochemical method of making hybrid metal-polymer microparticles in an aqueous, biocompatible solution by providing a metal (I) composition and one or more polymeric materials; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration.

22 Claims, 30 Drawing Sheets

(56) References Cited

OTHER PUBLICATIONS

Hu, et al., "A New Route to Crystalinne Hydrogels, Guided by a Phase Diagram" Chem. Int. Ed. Oct. 13, 2003, 42:39, 4799-4802.

Huang et al. "Chitosan mediated assembly of gold nanoparticles multilayer", Colloids and Surfaces. A: Physicochem. Eng. Aspects Sep. 30, 2003, 226:1-3, 77-86.

Huang et al., "Cancer Cell Imaging and Photothermal Therapy in the Near-Infrared Region by Using Gold Nanorods," J. Am. Chem. Soc. 2006, 128, 2115-2120.

Jana et al. "Wet chemical synthesis of silver nanorods and nanowires of controllable aspect ratio," Chem. Commun. 2001, 7, 617-618.

Jiang et al. "Thermoresponsive hydrogel of Poly (glycidyl methacrylate-co-N-isopropylacrylamide) as a Nanoreactor of gold nanoparticles", J. Poly. Sci. A:Poly.Chem. Jul. 1, 2007, 45, 2812-2819.

Kim et al. "Thermo- and pH—Responsive Hydrogel-coated Gold Nanoparticles" Chem. Mater. 2004, 16, 3647.

Kumar et al, "Plasmonic Nanosensors for Imaging Intracellular Biomarkers in Live Cells," Nano Lett. 2007, 7:5, 1338-1343.

Ohnuma, A. et al., "Metal-polymer hybrid colloidal particles with an eccentric structure" Langmuir, 2009, vol. 25, No. 24. pp. 13880-13887.

Lee, T.R. et al. "Hydrogel-Templated growth of large gold nanoparticles: Syntheses of thermally responsive hydrogel-Nanoparticle composites", Langmuir, 2007, 23, 6504.

Lu et al. "Environmentally friendly syntheses of highly monodisperse biocompatible gold nanoparticles with urchin-like shape", Langmuir 2008, 24:3 1058-1063.

Marpu. S. B., 'Biocompatible hybrid nanomaterials involving polymers and hydrogels interfaced with phosphorescent complexes and toxin-free metallic nanoparticles for biomedical applications , Dissertation, University of North Texas. Aug. 2011. See pp. 130-266, 273-278, and 355-356.

Metraux et al., "Rapid Thermal Synthesis of Silver Nanoprisms with Chemically Tailorable Thickness" Adv. Mat. Feb. 2005, 17:4, 412-415.

Pardo-Yissar et al. "Gold nanoparticles/hydrogel composites with solvent-switchable electronic properties", Adv. Mat. Sep. 2001, 13:17, 1320-1323.

Seo et al., "FeCo/graphitic-shell nanocrystals as advanced magnetic-resonance-imaging and near-infrared agents," J. Am. Chem. Soc. 2006, 128, 2115-2120.

Sperling et al., "Biological applications of gold nanoparticles," Chem. Soc. Rev. 2008, 37, 1896-1908.

Sugunan et al. "Heavy-Metal ion sensors using Chitosan-capped gold nanoparticles", Science and Technology of Adv. Mat. 2005, 6, 335.

Zhao et al. "Thermoswitchable Electronic Properties of a gold Nanoparticle/ Hydrogel Composite", Macromol. Rapid Commun. Nov. 14, 2005, 26:22, 1784-1787.

Zhao et al. "A kind of smart gold nanoparticles-hydrogel composite with tunable thermo-switchable electrical properties", New J. Chem. 2006, 30, 915.

Zhu et al., "Preparation of silver nanorods by electrochemical methods" Materials Letters. Jun. 2001, 49:2, 91-95.

PCT/US2013/035493 International Search Report (Corrected Version) [KIPO] dated Jul. 26, 2013.

\* cited by examiner

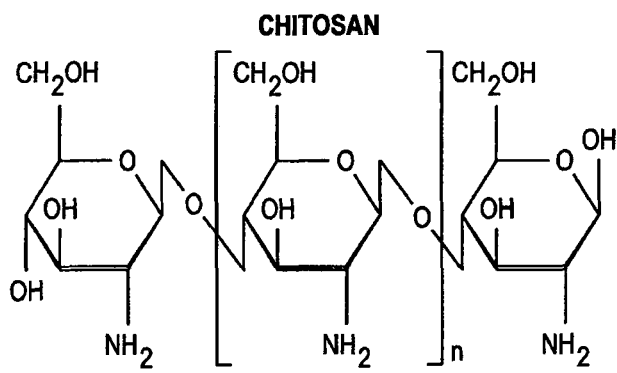
FIG. 3a
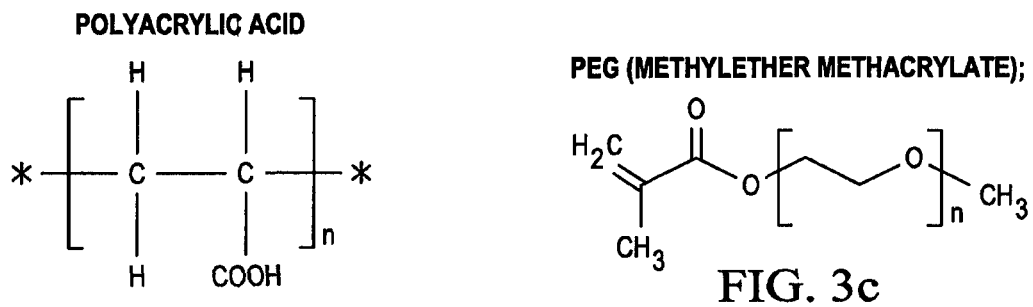
FIG. 3b
FIG. 3c
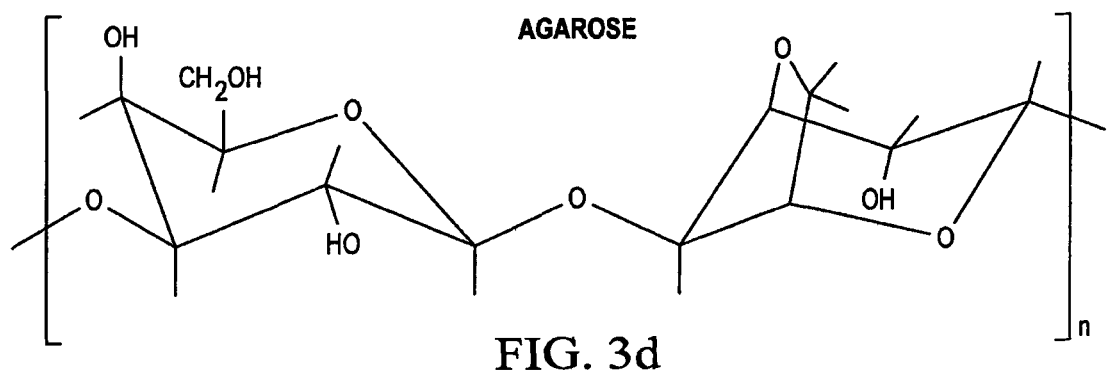
FIG. 3d
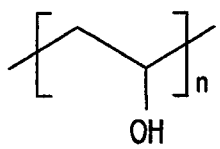
FIG. 3e

| | r(0), nm | r(30), nm | r(60), nm | %r(30)/ r(0) | %r(60)/ r(0) | %D(30) | %D(60) | f(30) | f(60) |
|---|---|---|---|---|---|---|---|---|---|
| CONTROL | 111 | 108 | 108 | 97.30% | 97.30% | 2.70% | 2.70% | 1.00 | 1.00 |
| Nanocomposite_Cycle1 | 146 | 127 | 105 | 86.99% | 71.92% | 13.01% | 28.08% | 4.82 | 10.39 |
| Nanocomposite_Cycle2 | 136 | 110 | 94 | 80.88% | 69.12% | 19.12% | 30.88% | 7.07 | 11.43 |

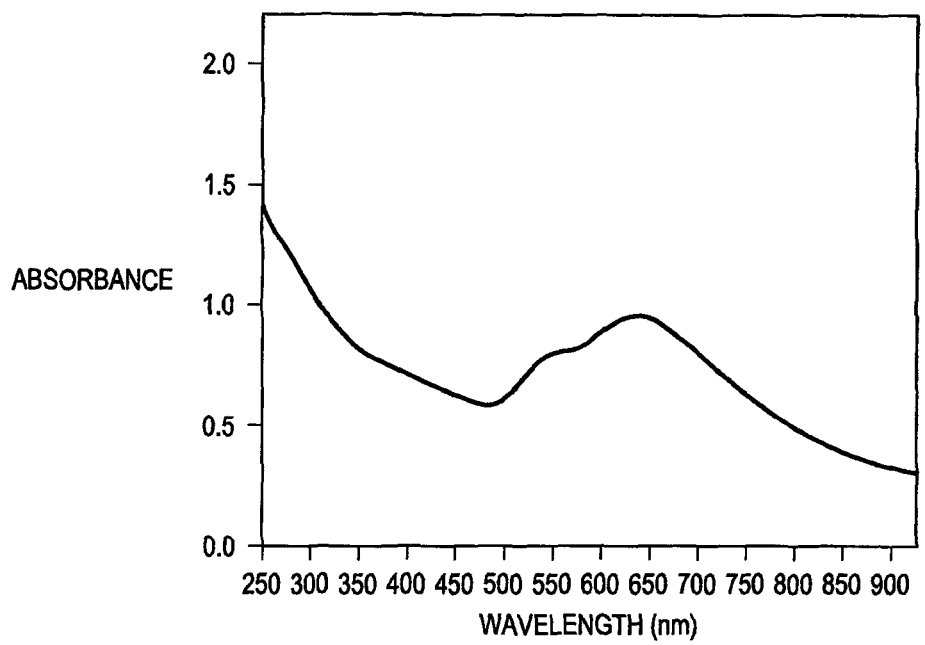
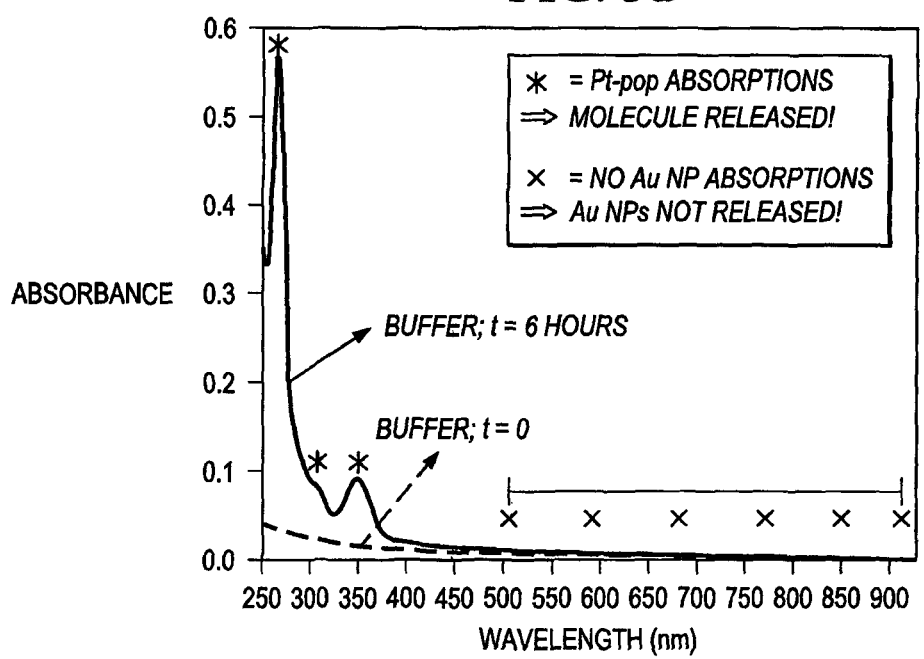

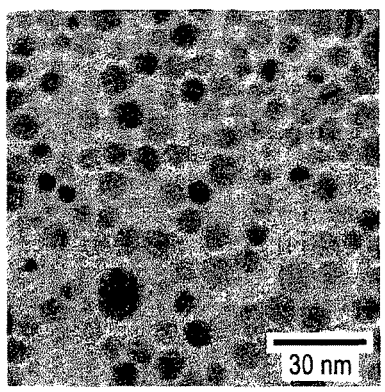

FIG. 8a

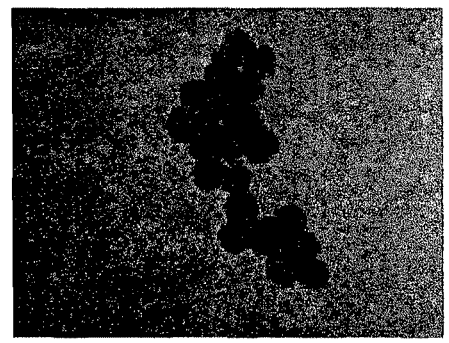

FIG. 8b

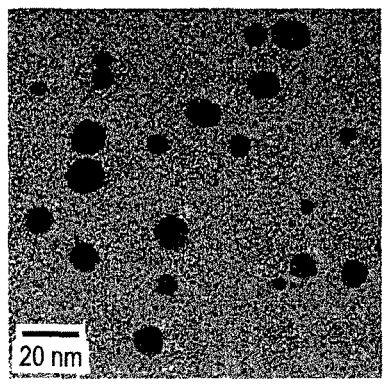

FIG. 8c

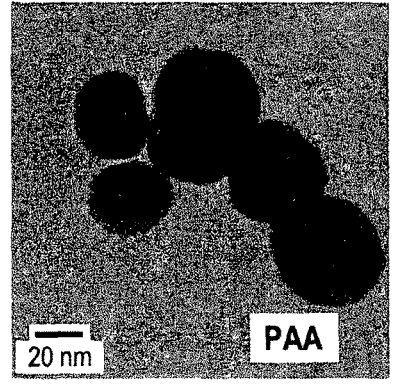

FIG. 8d

| METHOD | FOR SPHERICAL AgNPs | FOR NEAR IR ABSORBING PARTICLES | CHEMICALS |
|---|---|---|---|
| CONVENTIONAL | GLYCOLS, NaBH$_4$ | COMBINATION OF NaBH$_4$, ASCORBIC ACID | REDUCING AGENT |
| | SODIUM CITRATE, TERTIARY AMINE BASED SURFACTANTS AND POLYMERS | CTAB, PVP, SDS | STABILIZING AGENTS |
| | YES | LIGHT (BUT START FROM SILVER NANOSPHERS, USE DESIGNED FILTERS) | LIGHT (AS REDUCING AGENT) |
| DISCLOSURE METHOD | LIGHT, SUNLIGHT | LIGHT, SUNLIGHT | REDUCING AGENT |
| | BIOCOMPATIBLE POLYMERS, FIBER POLYMERS, GELS | | STABILIZING AGENT |

FIG. 8e

TESTING LEACHING OF AgNPs FROM NYLON MATRIX

WEAK ABSORPTION FROM HOT WATER SAMPLE INDICATES A SMALL DEGREE OF LOSS OF SOME UNREACTED $Ag^+$ IONS OR WEAKLY-ADSORBED AgNPs INTO THE HOT WATER DURING THE INITIAL STAGES

FACILE METHOD FOR MAKING NON-TOXIC BIOMEDICAL COMPOSITIONS COMPRISING HYBRID METAL-POLYMER MICROPARTICLES

CROSS-REFERENCE TO RELATED APPLICATIONS

This Non-Provisional Patent Application claims is a national stage filing of PCT/US/2013/035493, filed on Apr. 5, 2014 and claims priority to U.S. Provisional Patent Application Ser. No. 61/621,148, filed Apr. 6, 2012, the contents of which is incorporated by reference herein in its entirety.

TECHNICAL FIELD OF THE INVENTION

The present invention relates in general to the field of hybrid metal-polymer microparticle synthesis and in particular, methods of synthesizing nanoparticles using environmentally benign non-toxic materials for stabilization in aqueous media toward use in pharmaceutical and biological applications.

BACKGROUND ART

Plasmonic nanoparticles are a special class of nanomaterials that have significant impacted both applications and scientific understandings in diverse fields including catalysis, bio-chemical detection, luminescence and wide range of other biomedical applications. These metallic nanoparticles made from different physical and chemical techniques result in broad size, shape and compositions depending on nature of method employed for syntheses. For many optoelectronic and biological applications tuning of plasmon absorption in the Near-Infrared is desired and achieved by growth techniques based on photochemical and thermal reduction involving clustering of smaller particles in to larger anisotropic nanostructures.

Size and plasmon absorption are important parameters in metallic nanoparticles and control over size and plasmon absorption results in a variety of nanostructures with controllable aspect ratios; however, less is known about controlling size, shape or tuning plasmon absorption in absence of reducing agents in combination with bio compatible polymers or gels for optimizing biological applications of these metallic nanoparticles.

DISCLOSURE OF THE INVENTION

The present invention relates to silver nanospheres and/or anisotropic shape particles using light as a reducing agent that avoids syntheses and using extra reducing agents. As such, the present invention facilitates formation of anisotropic hybrid silver-polymer microparticles in single step which is unexplored before the present invention. All "bottom up" solution based syntheses techniques in the art currently are multi-step protocols especially for making anisotropic hybrid silver-polymer microparticles; involving usage of definite reducing agents.

The present invention provides a method of altering the conditions to make anisotropic hybrid silver-polymer microparticles in a single step in the complete absence of regular reducing agent, without having started with silver nanospheres as initiators. The present invention provides the use of a wide variety of polymers including both biologically useful polymers (e.g., chitosan, alginic acid, and HPC) and industrially useful polymers (e.g., Nylon, polyurethane, and PAN).

The present invention provides a method of making a pharmaceutical hybrid metal-polymer microparticle composition for the delivery of an active agent comprising the steps of: forming hybrid metal-polymer microparticles with a tunable NIR plasmon absorption in an aqueous, biocompatible solution by providing an aqueous biocompatible solution; combining a metal (I) composition and one or more polymeric materials in the aqueous biocompatible solution; applying an electromagnetic radiation to the metal (I) composition to convert the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration and provide the NIR plasmon absorption of the one or more hybrid metal-polymer microparticles between 700 nm-1200 nm; and adding one or more active agents to the stabilized one or more hybrid metal-polymer microparticles to form a pharmaceutical hybrid metal-polymer microparticle composition. The present invention also provides the composition made by this method.

The present invention provides a method of making a hybrid metal-polymer microparticle diagnosis complex comprising the steps of: forming a hybrid metal-polymer microparticles with a tunable NIR plasmon absorption in an aqueous, biocompatible solution by providing an aqueous biocompatible solution; combining a metal (I) composition and one or more polymeric materials in the aqueous biocompatible solution; applying an electromagnetic radiation to the metal (I) composition to convert the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration and provide the NIR plasmon absorption of the one or more hybrid metal-polymer microparticles between 700 nm-1200 nm; and adding one or more binding agents to the stabilized one or more hybrid metal-polymer microparticles to form a diagnosis complex that binds to a specific agent. The present invention also provides the composition made by this method.

The present invention provides a method of making a hybrid metal-polymer microparticle composition for the detection of small molecules comprising the steps of: forming a hybrid metal-polymer microparticle with a tunable NIR plasmon absorption in an aqueous, biocompatible solution by providing an aqueous biocompatible solution; combining a metal (I) composition and one or more polymeric materials in the aqueous biocompatible solution; applying an electromagnetic radiation to the metal (I) composition to convert the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration and provide the NIR plasmon absorption of the one or more hybrid metal-polymer microparticles between 700 nm-1200 nm; and adding one or more agents that interact to identify the one or more small molecules using surface enhanced Raman scattering. The present invention also provides the composition made by this method.

The present invention provides a method of making an imaging hybrid metal-polymer microparticle composition for imaging a portion of a cell comprising the steps of: forming a hybrid metal-polymer microparticles with a tunable NIR plasmon absorption in an aqueous, biocompatible solution by providing an aqueous biocompatible solution; combining a metal (I) composition and one or more polymeric materials in the aqueous biocompatible solution; applying an electromagnetic radiation to the metal (I) composition to convert the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration and provide the NIR plasmon absorption of the one or more hybrid metal-polymer microparticles between 700 nm-1200 nm; and adding one or more agents that interact with a portion of a cell to the stabilized one or more hybrid metal-polymer microparticles form a imaging hybrid metal-polymer microparticle composition. The present invention also provides the composition made by this method.

The present invention provides a hybrid metal-polymer microparticle nanofiber composite made by the process comprising the steps of: providing an aqueous biocompatible solution; combining a metal (I) composition, one or more polymeric materials and one or more nanofibers; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; stabilizing the one or more hybrid metal-polymer microparticles with the one or more polymeric materials to prevent agglomeration; forming a hybrid metal-polymer microparticle nanofiber composite; and tuning of a NIR plasmon absorption of the one or more hybrid metal-polymer microparticles between 700 nm-1200 nm by varying time of exposure, concentrations of the one or more polymeric materials, concentrations of the metal (I) composition or a combination thereof. The metal (I) composition may be silver to form an antipathogenic biocompatible polymer composition. The one or more polymer stabilizers comprises agarose, hydrogels, PAA (poly acrylic acid), PVA (poly vinyl alcohol), Chitosan, PNIPAM (Poly-N-isopropyl acrylamide), substituted PNIPAM (including PNIPAM-aa (poly-N-isopropyl acrylamide-acrylic acid), PNIPAM-allylamine (Poly-N-isopropyl acrylamide-allylamine), and PNIPAM-SH), PAMAM (Polyamidoamine), PEG (Poly ethylene glycol), alginic acid, HPC (hydroxyl propyl cellulose), or a combination thereof. The hybrid metal-polymer microparticle nanofiber composite may be formed into a filter, a textile, a fiber, a cloth or similar material. The hybrid metal-polymer microparticle nanofiber composite may be made into a filter, a water filter, a textile, a fiber, or a similar material.

In addition, the present invention provides for the instantaneous formation of hybrid silver-polymer microparticles, doped gels and films in a wide variety of polymers. In contrast, the formation of hybrid silver-polymer microparticles loaded films and gels are generally two step methods, e.g., first hybrid silver-polymer microparticles are formed then doped in to films and gels.

The present invention provides a method and composition for the formation of anisotropic hybrid silver-polymer microparticles in a one-step non-seeded approach using biologically and environmental sensitive polymers, e.g., chitosan or alginic acid. In addition, the present invention provides antibacterial activity using silver nanospheres and anisotropic nanoparticles. Hybrid silver-polymer microparticles doped nanofibers are used for many biomedical applications; however, retaining the hybrid silver-polymer microparticles after washing is a big issue. The present invention provides retainment of hybrid silver-polymer microparticles after detergent washings. In addition, hybrid silver-polymer microparticles are highly sensitive and tend to decompose with time making them difficult to store or transport. The present inventors discovered that in film form, the nanoparticles are stable for years and on redispersion these films retain original solution properties.

Hybrid silver-polymer microparticles are uniquely famous for antibacterial/antifungal/antipathogenic properties. These properties make hybrid silver-polymer microparticles doped polymers/fibers/materials for various biomedical applications. Plasmon absorption property of hybrid silver-polymer microparticles is utilized in solar cell or conductive coating industrial applications. The present invention provides the feasibility to work with broad range of polymers and gels which have strong environmental/biological importance.

The present invention demonstrates unique formation of nanoparticles doped nanofibers of significant applications in water filtration, sensing, protection and textile applications. The present technology provides unique feasibility in integrating different size gold and hybrid silver-polymer microparticles directly on to nanofibers selected from industrial important polymers Nylon, Polyurethane, Polyacrylonitriles.

The present invention relates to formation and stabilization of silver nanocomposites within matrix of both environmentally benign non-toxic materials like Chitosan, PAA (Poly-acrylic acid), Alginic acid, PVA (poly vinylalcohol), PEG (polyethylene glycol), PAMAM (Polyamidoamine) and HPC (hydroxyl propylcellulose) polymers and also in presence of special polymers like nylon, polyurethane and polyacrylonitrile. The present invention uses both aqueous and organic solvents as reaction medium depending on application interest but in complete absence of any reducing agents in a single step. In contrast to the methods in the art for formation of Near Infrared absorption hybrid silver-polymer microparticles, the present invention provides a facile single-step method involving significantly no chemicals except for silver salt as precursor coupled with stabilizing polymers. For example, literature methods to produce Near Infrared absorbing particles involve either of these or combination of chemicals including CTAB (stabilizer), $NaBH_4$ (reducing agent), and PVP some of which are already know to be toxic.

Entrapping hybrid silver-polymer microparticles within different fiber materials for making antimicrobial clothes is a recent surge in hybrid silver-polymer microparticles research but most of the literature protocols follow two step method. Sodium citrate stabilized hybrid silver-polymer microparticles are doped in to fiber material of choice or fiber materials are doused with metal salts followed by an addition of reducing agents. In both, these above methods usage of reducing agent is unavoidable. In contrast, the present embodiment discusses entrapping hybrid silver-polymer microparticles within polymer of choice in complete absence of any reducing agent. Distinguished innovative idea of present invention allows tuning of NIR plasmon absorption of hybrid silver-polymer microparticles anywhere between 700 nm-1200 nm in a single-step just by varying time of exposure and concentrations of biopolymer and silver salt. Specifically, the method renders the route for spontaneous formation of hybrid silver-polymer microparticles with plasmon absorption tunable between visible and Near Infrared region by varying pH of the medium, and the light exposure conditions in combination with variations in nature of glass used for performing reaction which is unprecedented approach in literature.

The instant invention provides a method of synthesizing nanoparticles using environmentally benign non-toxic materials for stabilization in aqueous media toward use in pharmaceutical and biological applications. The preparation of hybrid metal-polymer microparticles in this invention involves only environmentally benign, biocompatible and/or non-toxic materials.

In contrast to the methods used in the prior art, the syntheses method of the present invention of NIR-absorbing hybrid gold-polymer microparticles is a facile single-step method and involves significantly fewer chemicals compared to methods in the literature. Chemicals in literature methods including CTAB (stabilizer), $NaBH_4$ (reducing agent), $AgNO_3$ and CDAB (growth enhancers) are very toxic to both human cells and the environment. Environmental concerns and cell toxicity are of major concern in the chemicals used in the literature synthesis methods, which are not used in this invention. Minimizing the use of chemicals and effective replacement of these chemical ligands with biologically adaptable biomolecules will enhance all biological applications of hybrid gold-polymer microparticles. The present invention allows the syntheses of NIR-absorbing hybrid gold-polymer microparticles with about 700-1200 nm plasmon absorptions in a single-step from a single starting precursor.

The present invention provides a photochemical method of making hybrid metal-polymer microparticles in an aqueous, biocompatible solution by providing a metal (I) composition and one or more polymeric materials; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration.

The metal (I) composition can be a gold (I) complex, silver (I) complex or salt, copper (I) complex or salt, or combinations thereof. The metal (I) can be a metal selected from the group consisting of titanium, gold, platinum, palladium, nickel, silver, copper or manganese. The metal (0) can be at least one metal atom selected from the group consisting of aluminum, antimony, arsenic, barium, beryllium, bismuth, cadmium, calcium, cerium, chromium, cobalt, copper, dysprosium, erbium, europium, gadolinium, gallium, gold, hafnium, holmium, indium, iridium, iron, lanthanum, lead, lithium, lutetium, magnesium, manganese, mercury, molybdenum, neodymium, nickel, niobium, osmium, palladium, platinum, potassium, praseodymium, rhenium, rhodium, rubidium, ruthenium, samarium, scandium, silver, strontium, tantalum, technetium, terbium, titanium, thallium, thorium, thulium, tin, tungsten, uranium, vanadium, ytterbium, yttrium, zinc, and zirconium. The metal (I) precursor can be Au(tetrahydrothiophene)Cl, $AuMe2SCl$, Au(CO)Cl, $AgNO_3$ or $AgPF_6$. The electromagnetic radiation is UV light, Sunlight, microwave radiation, far infrared radiation, near infrared radiation, visible radiation, ultraviolet radiation, x-rays, gamma rays, or high-energy gamma rays. The one or more polymeric materials can be Chitosan, Polyacrylic acid, Alginic acid, PEG, PVA, Agarose, HPC, NIPA, Nylon, polyurethane, or polyacrylonitrile. The one or more polymer stabilizers can be agarose, hydrogels, PAA (poly acrylic acid), PVA (poly vinyl alcohol), Chitosan, PNIPAM (Poly-N-isopropyl acrylamide), substituted PNIPAM (including PNIPAM-aa (poly-N-isopropyl acrylamide-acrylic acid), PNIPAM-allylamine (Poly-N-isopropyl acrylamide-allylamine), and PNIPAM-SH), PAMAM (Polyamidoamine), PEG (Poly ethylene glycol), alginic acid, HPC (hydroxyl propyl cellulose), or a combination thereof. The method further includes the step of controlling the sizes of the one or more hybrid metal-polymer microparticles by modifying the reaction conditions, one or more polymeric materials, or the starting materials and controlling the shape of the one or more hybrid metal-polymer microparticles by modifying the reaction conditions, one or more polymeric materials, or the starting materials. The step of converting includes the photoreduction reaction to convert the metal (I) to the metal (0).

The one or more polymeric materials may be Chitosan, Polyacrylic acid, Alginic acid, PEG, PVA, Agarose, BSA, albumin, bovine serum albumin, human albumin, synthetic albumin, HPC, PNIPA, Nylon, polyurethane, or polyacrylonitrile. In one example the metal (I) is silver and the one or more polymeric materials comprise Nylon, polyurethane, or polyacrylonitrile.

The present invention includes stabilization of different size hybrid gold-polymer microparticles directly in to biologically significant polymers like BSA (Bovine Serum Albumin) and including albumin, bovine serum albumin, human albumin, synthetic albumin. The steps of conversion from metal (I) to metal (0) are brought either by photoreduction or thermal reduction or under ambient conditions.

The present invention includes a hybrid metal-polymer microparticle made by the process comprising the steps of: providing a metal (I) composition and one or more polymeric materials; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration. The invention includes the step of conjugating the one or more hybrid metal-polymer microparticles to an active agent to form a site specific active agent delivery complex and of conjugating the one or more hybrid metal-polymer microparticles to a binding agent for use as a diagnosis complex.

The present invention includes a method of tuning the plasmon absorption energies and intensities and corresponding variation of the size and shape of hybrid metal-polymer microparticles by providing a metal (I) composition and one or more polymeric materials; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; stabilizing the one or more hybrid metal-polymer microparticles with the one or more polymeric materials to prevent agglomeration; and adjusting one or more parameters selected from pH, ionic strength, reaction time, irradiation time, temperature, centrifugation, sonication, reaction vessel material, optical filters, and combinations thereof, to adjust at least one of the tuning of the plasmon absorption energies or intensities and corresponding variation of at least one of size or shape of the one or more hybrid metal-polymer microparticles to adjust a plasmon absorption energy, an intensity or a combination thereof.

The present invention includes a method of treating a tissue by selecting a tissue in need of therapy; contacting the tissue with therapeutically effective amount of a hybrid metal-polymer microparticles made by: providing a metal (I) composition and one or more polymeric materials; applying an electromagnetic radiation to the metal (I) composition; converting the metal (I) composition to a metal (0) composition; forming one or more hybrid metal-polymer microparticles from the metal (0); capping the one or more hybrid metal-polymer microparticles; and stabilizing the one or more hybrid metal-polymer microparticles with the one or more polymeric materials to prevent agglomeration.

The hybrid metal-polymer microparticle composition may be varied in size, shape or both by varying the nature of the glass source or by modifying the reaction conditions, one or more polymeric materials, or the starting materials. The step of controlling one or more characteristics of the one or more hybrid metal-polymer microparticles may include adjusting one or more parameters selected from pH, ionic strength, reaction time, irradiation time, temperature, centrifugation, sonication, reaction vessel material, optical filters, and combinations thereof, to adjust at least one of the tuning of the plasmon absorption energies or intensities and corresponding variation of at least one of size or shape of the one or more hybrid metal-polymer microparticles to adjust a plasmon absorption energy, an intensity or a combination thereof. The hybrid metal-polymer microparticle composition is varied in NIR plasmon absorption by varying the nature of the glass source time of exposure and concentrations of the one or more polymeric materials and the metal (I) composition. The electromagnetic radiation may be UV light, Sunlight, microwave radiation, far infrared radiation, near infrared radiation, visible radiation, ultraviolet radiation, x-rays, gamma rays, or high-energy gamma rays.

The active agent may be an agent that binds a cell receptor, an enzyme active site, an antibody, a cell surface receptor, a small molecule, or other biological molecule. The active agent may be delivered by a phase transition changes in polymer nanoparticles, or bioconjugating drug molecules on to nanoparticles.

DESCRIPTION OF THE DRAWINGS

For a more complete understanding of the features and advantages of the present invention, reference is now made to the detailed description of the invention along with the accompanying figures and in which:

FIGS. 3a-3g show the structure of the benign biopolymer monomers whose structures are shown in FIG. 2.

FIGS. 8a-8d are images of nanoparticles.

FIG. 8e is a table of some embodiments of the preparation methods of the NPs of the present invention.

DESCRIPTION OF THE INVENTION

Figure 1:
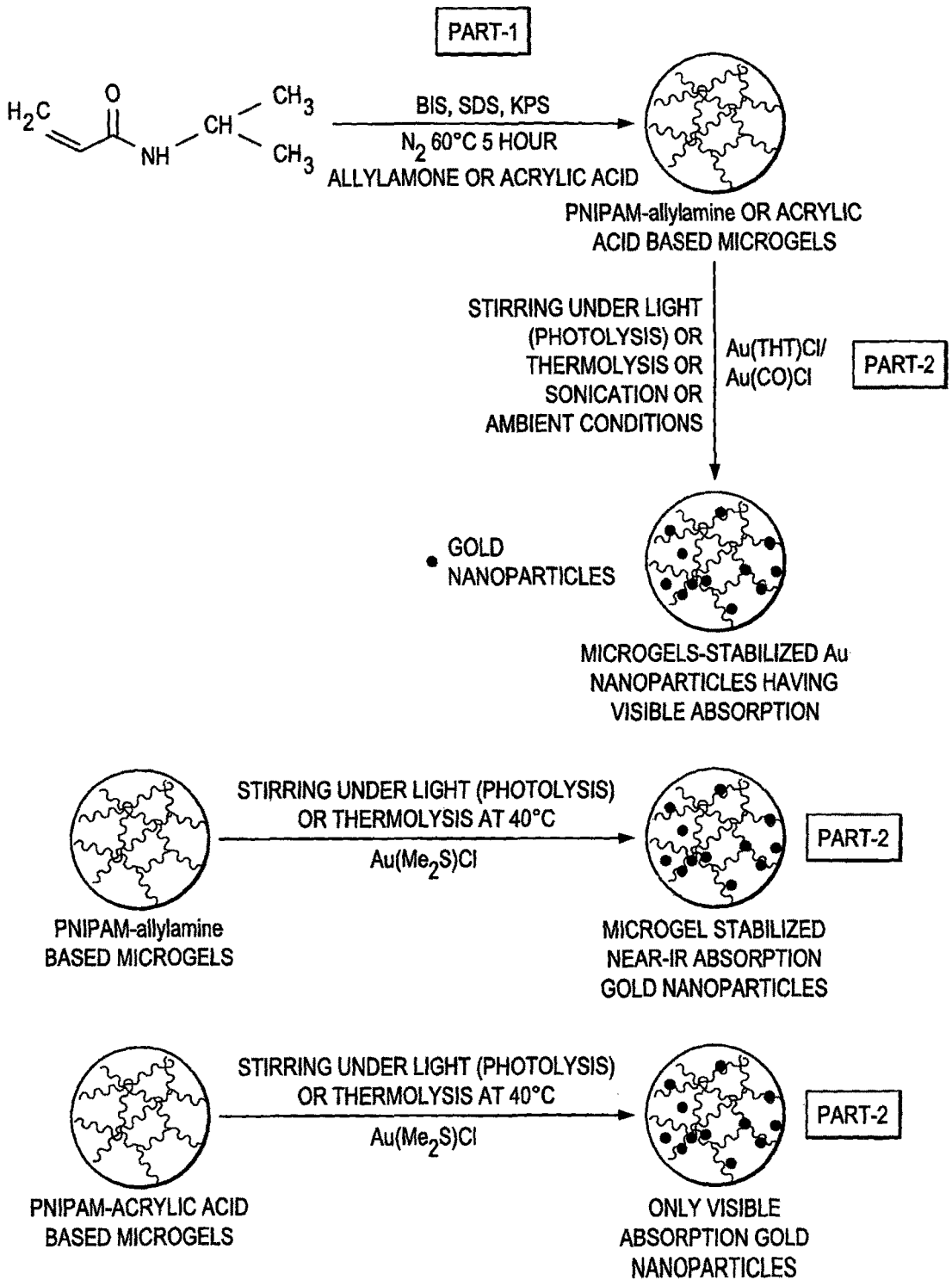
FIG. 1 is a schematic of the synthesis of hybrid gold-polymer microparticles stabilized within the representative biologically-benign polymer microgel PNIPAM.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Without limiting the scope of the invention, its background is described in connection with hybrid metal-polymer microparticle synthesis. The performance and function of metal nanostructures depends on size, shape, composition, and structure and have many uses in numerous fields; however, the synthesis of hybrid metal-polymer microparticles poses potential environmental and biological risks. The syntheses methods found in the literature generally involve the reduction of metal ions using reducing agents such as hydrazine, sodium borohydride ($NaBH_4$), and dimethyl formamide, which are highly reactive and toxic chemicals. Generally, the literature method for the synthesis of near-infrared (NIR)-absorbing hybrid gold-polymer microparticles is a 3-step process (*Chem. Mater.* 2003, 15, 1957): First, tetrachloroauric acid ($HAuCl_4$), cetyltrimethylammonium bromide (CTAB) and $NaBH_4$ are mixed to form a seed solution. Second, $HAuCl_4$, CTAB. benzyldimethylhexadecylammonium chloride (BDAC), ascorbic acid, and silver nitrate ($AgNO_3$) are used to form a growth solution. Third, the seed and growth solutions are mixed in fixed proportions. CTAB (stabilizer), $NaBH_4$ (reducing agent), $AgNO_3$ and CDAB (growth enhancers) are very toxic to both human cells and the environment. The contents of U.S. patent application Ser. No. 12/650,524 filed on Dec. 30, 2009 and U.S. Provisional Application No. 61/141,526 filed on Dec. 30, 2008.

As used herein the term nanoparticle, polymer nanoparticle, microparticle, polymer microparticle and hybrid metal-polymer microparticle can be used to denote a metallic particle that is encapsulated in a polymeric particle and the whole particle size is within 0.1-100 micron (micrometer) order of magnitude length scale. The particles can be 0.01 to 1000 micrometer and any incremental variation thereof.

The invention relates to syntheses of gold colloidal nanoparticles in aqueous media. The gold colloidal nanoparticles produced by the instant invention provide unique optical, electronic and molecular recognition properties that make them suitable agents for various biological applications. The prior art for gold colloidal nanoparticles synthesis procedures uses the Au(III) species $HAuCl_4$ as the starting precursor for the syntheses of gold colloidal nanoparticles and requires the aid of strong chemical reducing agents like $NaBH_4$ to reduce Au(III) to Au(0), which is then stabilized to prevent agglomeration by a variety of stabilizers that include polymers (e.g., PAA, Chitosan), gels (e.g., PNIPAM, PAMAM, or PEG), and surfactants (e.g., CTAB or BDAC). In contrast, the instant invention provides a method of synthesizing gold colloidal nanoparticles using Au(I) complexes such as Au(THT)Cl, $AuMe_2SCl$, and Au(CO)Cl as promising starting precursors for the syntheses of gold colloidal nanoparticles. The photoreduction and thermolysis reactions of the instant invention achieve this property due to the reduction of Au(I)→Au(0) in the precursors as compared to that from Au(III)→Au(0) in the prior art precursors. The instant invention provides tunable plasmon absorption capabilities across visible and NIR regions with emphasis on minimizing the use of potentially harmful chemicals like CTAB, $NaBH_4$, BDAC, and $AgNO_3$. This invention also teaches the syntheses of the gold colloidal nanoparticles without the aid of chemical reducing agents and under conditions that include photolysis, thermolysis, and stirring at ambient conditions. The instant invention includes biologically benign polymers that include Chitosan, agarose, PAA, PVA, along with "smart" thermo-responsive/stimuli-sensitive polymer hydrogels such as PNIPAM-aa and PNIPAM-allylamine as stabilizing agents for hybrid gold-polymer microparticles derived from Au(I) complexes as precursors. Although the instant example references hybrid gold-polymer microparticles, the skilled artisan will recognize that this applies to other metals that can be converted from a (I) state to a (0) state, e.g., silver.

As used herein, the term "aqueous" refers to a liquid mixture containing water, among other components.

As used herein, the term "bioactive agent" or "active agent" are used interchangeably and refer to a substance used in an application that is therapeutic in nature, such as methods for treating disease in a patient. Non-limiting examples of active agents include but are not limited to, anti-inflammatory agents, blood modifiers, anti-platelet agents, anti-coagulation agents, immune suppressive agents, anti-neoplastic agents, anti-cancer agents, anti-cell proliferation agents, and nitric oxide releasing agents, polynucleotides, polypeptides, oligonucleotides, gene therapy agents, nucleotide analogs, nucleoside analogs, polynucleic acid decoys, and therapeutic antibodies.

As used herein, the term "biocompatible" refers to the material, substance, compound, molecule, polymer, solutions, solvents, compositions, reagents or systems, which do not cause severe toxicity, severe adverse biological reaction, or lethality in an animal when administered at reasonable doses and rates. Typically, biocompatible materials are biologically inert and non-toxic in that they do not generate any immune and/or inflammatory reaction when provided to an organism such as an animal or human.

As used herein, the term "therapeutically-effective amount" refers to that amount of the nanoparticles of the present invention in an amount sufficient to modulate one or more of the symptoms of the condition or disease being treated (with or without additional therapeutic intervention, e.g., infrared energy directed at a target site or loading the nanoparticles with an active agent). A "therapeutically effective amount" and/or dosage range of the nanoparticles of the present invention used in the method of treatment of the invention may be determined by one of ordinary skill in the art via known criteria including target tissue, age, weight, and response of the individual patient, and interpreted within the context of the disease being treated and/or prevented.

The hybrid metal-polymer microparticles synthesized by the method of the instant invention may be used for site specific drug delivery devices where hybrid gold-polymer microparticles are bio-conjugated to drugs or other active agents and then released at specific sites of interest by various mechanisms such as photothermal volume phase transitions.

The hybrid metal-polymer microparticles synthesized by the method of the instant invention may also be used for surface enhanced Raman scattering (SERS) as diagnostic tools for the detection of small molecules, distinguishing cancerous cells from non-cancerous cells as a result of the strong scattering of hybrid gold-polymer microparticles by their binding to specific antibodies that bind only to cancerous cells. In addition, the hybrid gold-polymer microparticles can be conjugates to oligonucleotides for use as a detectable signature for detection of precise DNA sequence. Furthermore, the hybrid metal-polymer microparticles may be used for immunolabelling; imaging of cells and biomolecules; and recognition of proteins based on the interactions between hybrid metal-polymer microparticles—antibody conjugates (e.g., specifically hybrid gold-polymer microparticles—antibody conjugates) and their corresponding antigens.

The present invention provides a method of making hybrid gold-polymer microparticles (Au NPs) from common starting materials of Au(I) complexes (e.g., Au(Me$_2$S)Cl, Au(THT)Cl, and Au(CO)Cl, where Me$_2$S is dimethyl sulfide and THT is tetrahydrothiophene) in aqueous media that include biocompatible polymers and hydrogels (e.g., PNIPAM=poly(N-isopropylacrylamide), Chitosan, agarose, and poly(acrylic acid)).

The present invention also provides stable hybrid gold-polymer microparticles that have non-agglomerating behavior on storage at ambient conditions, as deduced from persistence of the physical color of the samples without precipitation, the absorption spectra, and TEM and SEM images.

In one embodiment, the present invention includes compositions and methods of making hybrid metal-polymer microparticles comprising the steps of: converting a metal (I) to a metal (0); forming one or more hybrid metal-polymer microparticles from the metal (0); and stabilizing the one or more hybrid metal-polymer microparticles with one or more polymer stabilizers to prevent agglomeration. In one aspect, the metal (I) precursor is a gold (I) complex, silver (I) complex or salt, copper (I) complex or salt, or combinations thereof. In another aspect, the metal (I) comprises Au(THT)Cl (where THT=tetrahydrothiophene), AuMe$_2$SCl, or Au(CO)Cl. In another aspect, the step of converting comprises photoreduction reaction, thermolysis reaction or both to convert the metal (I) to the metal (0). In another aspect, the one or more stabilizers comprise one or more polymers, one or more gels, one or more surfactants, or a combination thereof. In another aspect, the one or more stabilizers comprise or are selected from agarose, hydrogels, PAA (poly acrylic acid), PVA (poly vinyl alcohol), Chitosan, PNIPAM (Poly-N-isopropyl acrylamide), PNIPAM-aa (poly-N-isopropyl acrylamide-acrylic acid), PNIPAM-allylamine (Poly-N-isopropylacrylamide-allylamine), PAMAM (Polyamidoamine), PEG (Poly ethyleneglycol), alginic acid, HPC (hydroxyl propylcellulose), or a combination thereof. In another aspect, the method further comprises the step of conjugating the one or more hybrid metal-polymer microparticles to an active agent to form a site specific active agent delivery complex.

Another embodiment of the present invention is a hybrid metal-polymer microparticle made by the process comprising the steps of: converting a metal (I) to a metal (0); forming one or more hybrid metal-polymer microparticles from the metal (0); and stabilizing the one or more hybrid metal-polymer microparticles with one or more polymeric stabilizers to prevent agglomeration, wherein the synthesis occurs in solvents, solutions and using materials that are biocompatible, non-toxic, or both. In one aspect, the method further comprises the step of conjugating the one or more hybrid metal-polymer microparticles to an active agent to form a site specific active agent delivery complex. In another aspect, the method further comprises the step of conjugating the one or more hybrid metal-polymer microparticles to a binding agent for use as a diagnosis complex. In one aspect, the one or more hybrid metal-polymer microparticles are used in surface enhanced Raman scattering for the detection of small molecules. In another aspect, the method further comprises the step of conjugating the one or more hybrid metal-polymer microparticles to a cell surface for cell imaging.

In another embodiment, the nanoparticles and methods of tuning the plasmon absorption energies and intensities and the corresponding variation of the size and shape of hybrid metal-polymer microparticles comprise the steps of: converting a metal (I) to a metal (0); forming one or more hybrid metal-polymer microparticles from the metal (0); adjusting one or more parameters selected from pH, ionic strength, reaction time, irradiation time, temperature, and combinations thereof to adjust the tuning of the plasmon absorption energies and intensities and corresponding variation of the size and shape of the one or more hybrid metal-polymer microparticles to adjust a plasmon absorption energy, an intensity or a combination thereof; and stabilizing the one or more hybrid metal-polymer microparticles with one or more stabilizers to prevent agglomeration. In one aspect, the step of converting comprises photoreduction reaction, thermolysis reaction or both to convert the metal (I) to the metal (0). In another aspect, the one or more stabilizers comprise one or more polymers, one or more gels, one or more surfactants, or a combination thereof. In another aspect, the one or more stabilizers comprises agarose, hydrogels, PAA (poly acrylic acid), PVA (poly vinyl alcohol), Chitosan, PNIPAM (Poly-N-isopropyl acrylamide), PNIPAM-aa (poly-N-isopropyl acrylamide-acrylic acid), PNIPAM-allylamine (Poly-N-isopropylacrylamide-allylamine), PAMAM (Polyamidoamine), PEG (Poly ethyleneglycol), HPC (hydroxyl propylcellulose), or a combination thereof. In another aspect, the method further comprises the step of conjugating the one or more hybrid metal-polymer microparticles to an active agent to form a site specific active agent delivery complex. In another aspect, the metal (I) comprises Au(THT)Cl (where THT=tetrahydrothiophene), AuMe$_2$SCl, or Au(CO)Cl. In another aspect, the one or more stabilizers comprise modified microgels comprising one or more functional groups. In another aspect, the metal (I) comprises a metal selected from the group consisting of titanium, gold, platinum, palladium, nickel, silver, copper or manganese. In another aspect, the metal (0) comprises at least one metal atom selected from the group consisting of aluminum, antimony, arsenic, barium, beryllium, bismuth, cadmium, calcium, cerium, chromium, cobalt, copper, dysprosium, erbium, europium, gadolinium, gallium, gold, hafnium, holmium, indium, iridium, iron, lanthanum, lead, lithium, lutetium, magnesium, manganese, mercury, molybdenum, neodymium, nickel, niobium, osmium, palladium, platinum, potassium, praseodymium, rhenium, rhodium, rubidium, ruthenium, samarium, scandium, silver, strontium, tantalum, technetium, terbium, titanium, thallium, thorium, thulium, tin, tungsten, uranium, vanadium, ytterbium, yttrium, zinc, and zirconium.

In another embodiment, the invention includes a method of making hybrid metal-polymer microparticles comprising the steps of: converting a metal (I) to a metal (0); forming one or more hybrid metal-polymer microparticles from the metal (0); and stabilizing the one or more hybrid metal-polymer microparticles with one or more stabilizers to prevent agglomeration, wherein the entire synthesis is performed using reagents and solutions that are biocompatible. In yet another embodiment, the present invention includes nanoparticles and methods of treating a tissue comprising: selecting a tissue in need of therapy; contacting the tissue with a therapeutically effective amount of hybrid metal-polymer microparticles made by: converting a metal (I) to a metal (0); forming one or more hybrid metal-polymer microparticles from the metal (0); and stabilizing the one or more hybrid metal-polymer microparticles with one or more stabilizers to prevent agglomeration, wherein the nanoparticles are produced with non-toxic materials that are biocompatible. In one aspect, the therapy is selected from photothermal therapy, and drug delivery.

The instant invention also provides a hybrid metal-polymer microparticle made by the process of converting a metal (I) to a metal (0) and forming one or more hybrid metal-polymer microparticles from the metal (0). The one or more hybrid metal-polymer microparticles are stabilizing with one or more stabilizers to prevent agglomeration. The present invention provides a method of tuning the plasmon absorption energies and intensities and corresponding variation of the size and shape of hybrid metal-polymer microparticles by converting a metal (I) to a metal (0) and forming one or more hybrid metal-polymer microparticles from the metal (0). One or more parameters selected from pH, ionic strength, reaction time, irradiation time, temperature, centrifugation, sonication, and combinations thereof are adjusted to adjust the tuning the plasmon absorption energies and intensities and corresponding variation of the size and shape of the one or more hybrid metal-polymer microparticles in order to adjust the plasmon absorption energy, intensity or a combination thereof. The one or more hybrid metal-polymer microparticles are stabilized with one or more stabilizers to prevent agglomeration. The present invention also provides a method for using hybrid metal-polymer microparticles produced from non-toxic materials for photothermal therapy, including cell killing and drug delivery.

In addition, the present invention provides Au(I) complexes to produce and tune the properties of hybrid gold-polymer microparticles stabilized in biologically-compatible media without adding chemical reducing agents or other toxic reagents. In contrast, all common preparation methods of hybrid gold-polymer microparticles known to the skilled artisan rely on chemical reduction of the Au(III) precursor tetrachloroauric acid ($HAuCl_4$) by adding a hazardous reducing agent such as $NaBH_4$; other harmful reagents such as CTAB=hexadecyltrimethlyammoniumbromide, BDAC benzyldimethylammoniumchloride, and silver nitrate ($AgNO_3$) are used to further grow the particle size (e.g., long nanorods) to make the hybrid gold-polymer microparticles absorb near-infrared (NIR) light, as needed for some biological applications. The instant invention does not utilize any of these harmful reagents. The instant invention provides a method of tuning the plasmon absorption energies and intensities and corresponding variation of the size and shape of the so formed hybrid gold-polymer microparticles by altering the reaction conditions, stabilizing biopolymer, and/or the starting Au(I) complex precursor. The instant invention provides a method of synthesizing hybrid gold-polymer microparticles starting from Au(I) precursor $Au(Me_2S)Cl$, which is available commercially. The synthesis of the stabilizing agent PNIPAM-co-allylamine (denoted henceforth as "PNIPAM-allylamine") or PNIPAM-co-acrylic acid (denoted henceforth as "PNIPAM-aa") microgels is based on a literature procedure (Hu, Z.; Gang, H.; Angew. Chem. Int. Ed. 2003, 42, 4799-4802). PNIPAM is known to the skilled artisan as representative biologically-benign polymer and include polymers of Chitosan, PAA, PEG, PVA, agarose, HPC, NIPA, which are available commercially. The syntheses of hybrid gold-polymer microparticles in microgels and different polymers involve the addition of 3.5-5 mg of the Au(I) precursor directly as a solid to the stirred solution of 0.2 weight percent microgel or 3-5 weight percent solution of different polymer solutions made by the addition of millipore water. The solution containing both the precursor and the stabilizing agent (e.g., PNIPAM microgel or another polymer) leads to the formation of hybrid gold-polymer microparticles under three conditions. The first condition is photolysis. Photolysis employs a UV photolysis lamp maintaining the temperature constant around 22° C. and using a cold water bath for about 20 minutes to initiate the formation of hybrid gold-polymer microparticles in solution; the change of color from colorless to violet/purple indicates formation of hybrid gold-polymer microparticles. The second condition is thermolysis where the same reaction can be performed by heating the complete reaction mixture to about 40° C. for 20 minutes. The third condition includes ambient conditions, where the reaction is also achievable simply by stirring the solution under ambient conditions of light and temperature for about 45 minutes. The completion of the reaction is indicated by the intense purple/violet color of the solution in about 45 minutes by photochemistry/thermochemistry and about 150 minutes under ambient conditions. Varying the starting Au(I) precursor changes the reaction times; for example, using Au(CO)Cl leads to instant formation of hybrid gold-polymer microparticles even under ambient conditions. The solutions are highly stable for long duration storage. The solutions can be centrifuged at 1000-1200 rpm for 5 minutes to remove any unreacted starting materials. Though the presence of the ligand $Me_2S$ (boiling point=38° C.) is debatable, it can be easily removed by heating the solution to the boiling point of the ligand, which leaves the hybrid gold-polymer microparticle solutions completely free of any unwanted hazardous materials while preserving the physical and chemical properties of colloidal hybrid gold-polymer microparticles without change. In the case of Au(CO)Cl, the dissociated ligand (CO) is a gas molecule so it evaporates in the hood even without heating. Absorption measurements in the UV/Vis/NIR region give primary information about the size range of the particles; SEM/TEM microscopy are then used to provide more accurate/quantitative information about the formation of hybrid gold-polymer microparticles with tunable size and shape, which can be controlled by experimental parameters such as the identity and concentration of the starting precursor and/or stabilizing agent.

In addition to preparation of biocompatible NIR (near infrared) gold and hybrid silver-polymer microparticles in perfect non-hazardous environment, the invention demonstrates utilization of these biocompatible nanoparticles with heat transducing properties for both delivery and photothermal applications using inexpensive light source compared to expensive medical lasers.

The hybrid gold-polymer microparticles of different sizes and shapes proposed in the present invention exhibited perfect non-toxic behavior under in vitro experimental testing conditions when compared with commercial analogues.

The hybrid gold-polymer microparticles of different sizes and shapes proposed in the present invention exhibited perfect non-toxic behavior under in vivio experimental testing conditions in zebra fish when compared with commercial analogues.

The hybrid silver-polymer microparticles of different sizes and shapes proposed in the present invention exhibited higher magnitude of antibacterial activity when tested in multiple pathogens in comparison with silver sulfadiazine drug.

The present invention provides a method of synthesizing hybrid gold-polymer microparticles. FIG. 1 is a schematic of the synthesis of hybrid gold-polymer microparticles stabilized within the representative biologically-benign polymer microgel PNIPAM. A biologically-benign polymer PNIPAM microgel spherical in shape is formed (e.g., PNIPAM-allylamine or PNIPAM-acrylic acid microgel) from the specific monomers. Au(Me$_2$S)Cl, Au(CO)Cl, or Au(THT)Cl is added to the microgel during stirring and under light (photolysis), heat (thermolysis), or ambient conditions to form PNIPAM microgel-stabilized hybrid gold-polymer microparticles. FIG. 1 illustrates in Part-1 the conditions for syntheses of PNIPAM-co-allylamine/acrylic acid based hydrogels. Part-2 describes syntheses of hybrid gold-polymer microparticles with visible or NIR absorption in the above microgel/hydrogel starting with Au(THT)Cl or Au(Me$_2$S)Cl as precursor under different possible conditions.

Figure 2A:
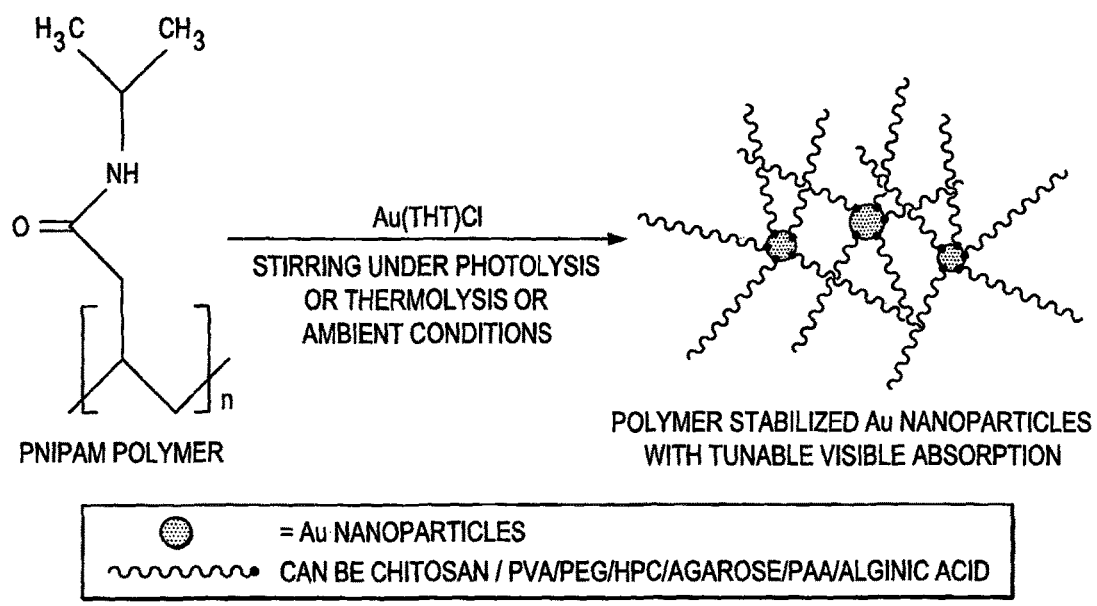
FIGS. 2a and 2b are schematics of the synthesis of hybrid gold-polymer microparticles stabilized within different commercially-available benign biopolymers and at different reaction conditions.
Figure 2B:
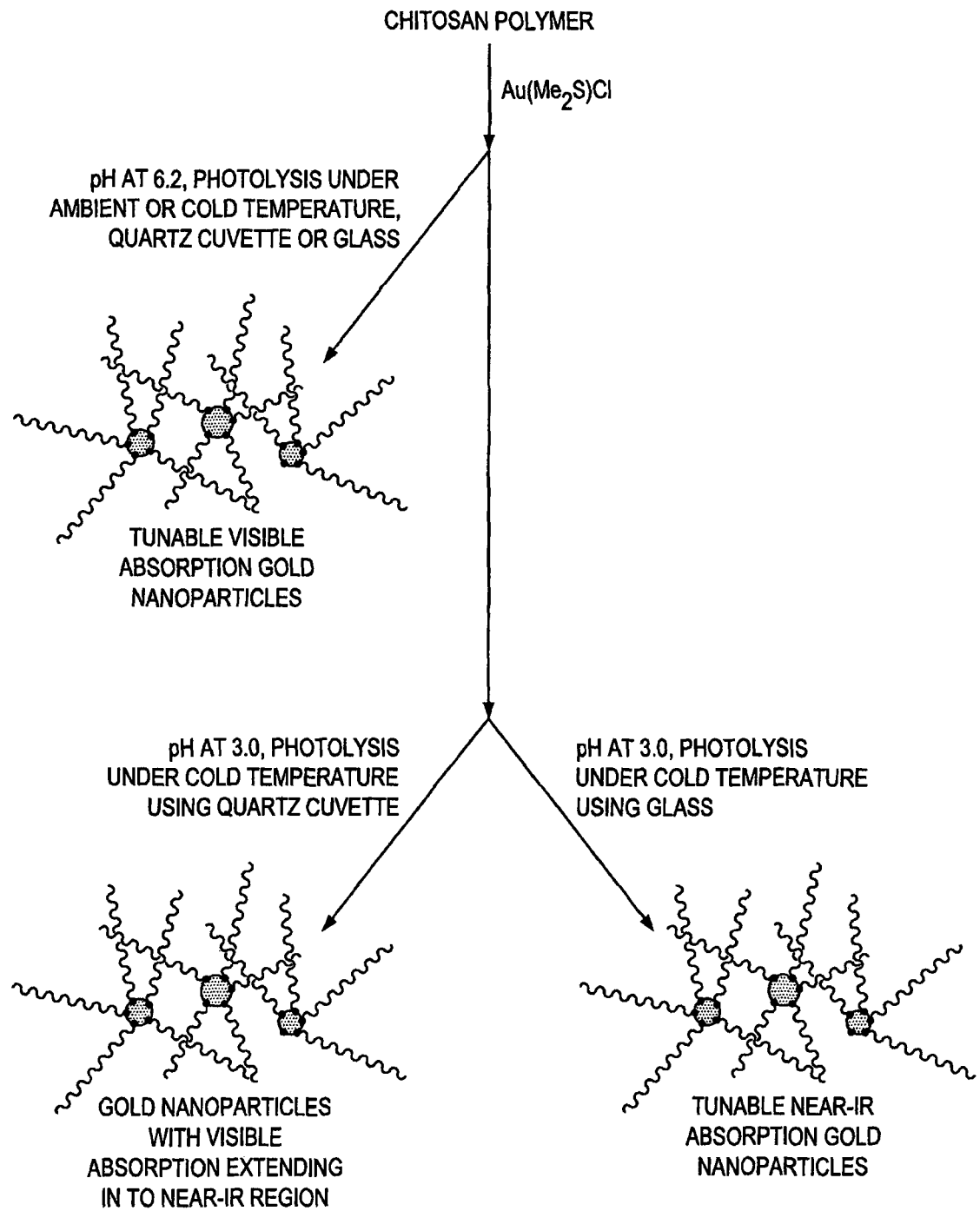
Figure 3F:
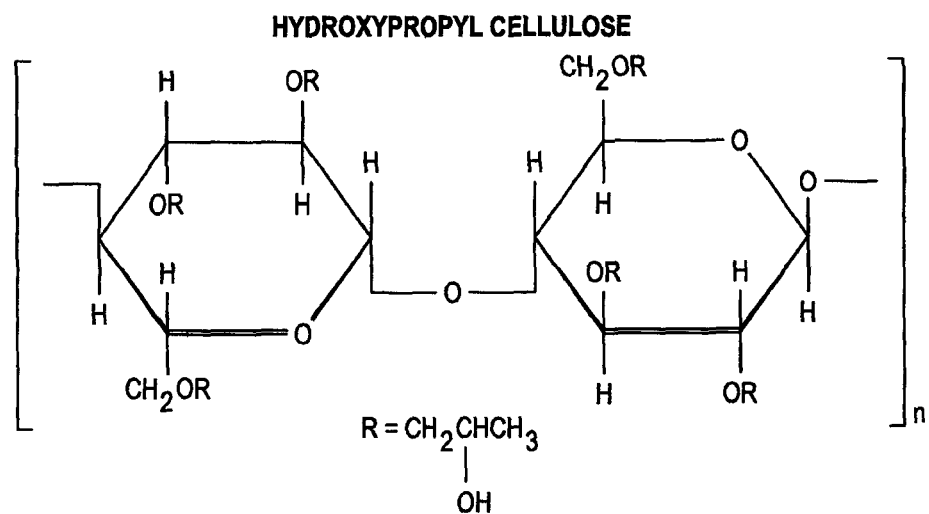
Figure 3G:
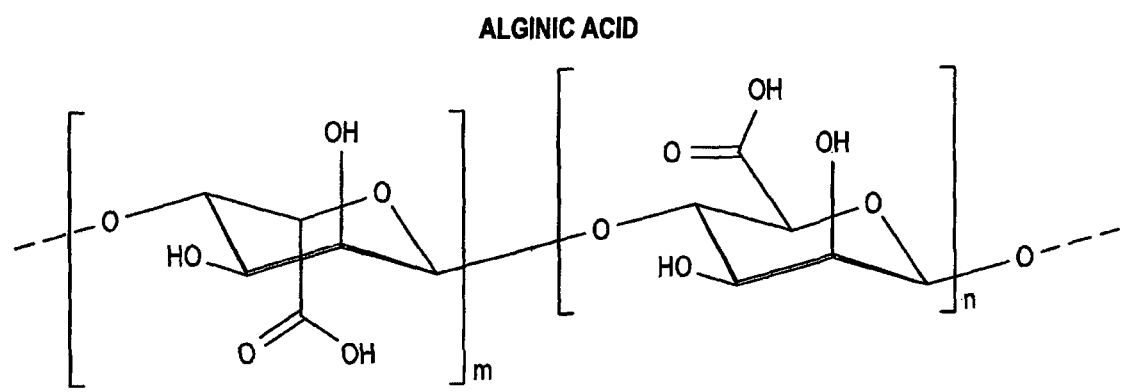
Figure 4A:
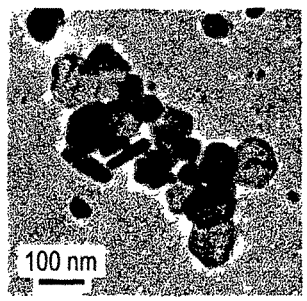
FIGS. 4a-4g are TEM and SEM images of the hybrid gold-polymer microparticles.
Figure 4B:
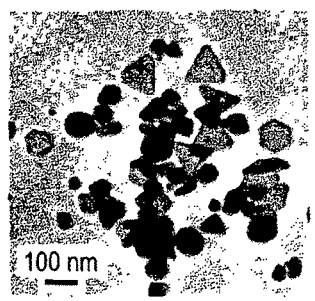
Figure 4C:
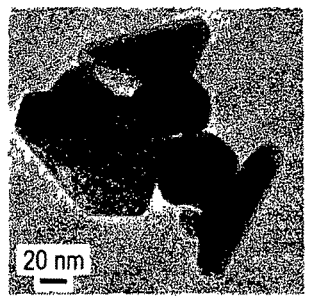
Figure 4D:
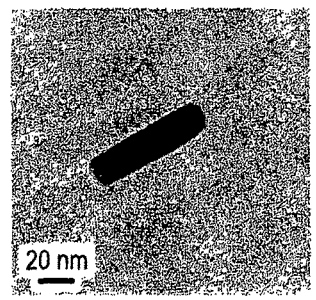
Figure 4E:
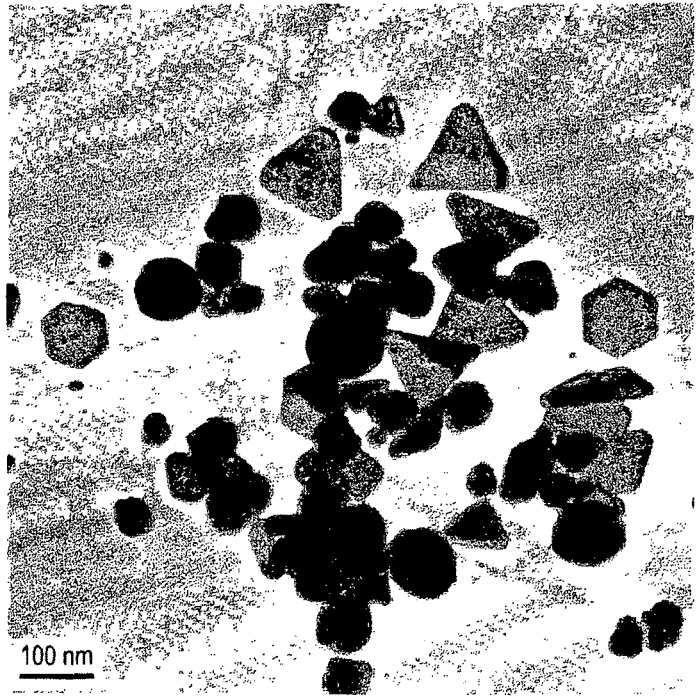
Figure 4F:
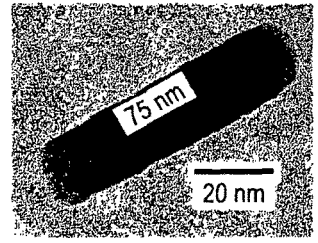
Figure 4G:
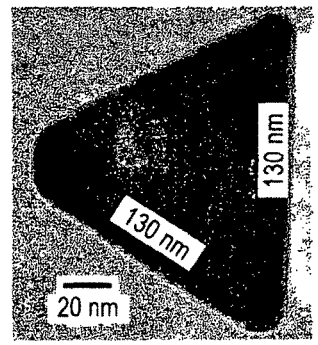

FIG. 2 is a schematic of the synthesis of hybrid gold-polymer microparticles stabilized within different commercially-available benign linear biopolymers under different experimental conditions. FIG. 2a shows the mechanism in such linear biopolymers whose structures are shown in FIGS. 3a-g while FIG. 2b illustrates the variability of some conditions during the synthesis. The relevant linear biopolymer may be mixed with Au(Me$_2$S)Cl, Au(CO)Cl, or Au(THT)Cl under conditions that include stirring under light (photolysis), heat (thermolysis), or ambient conditions to form polymer stabilized hybrid gold-polymer microparticles. The biopolymer can be seen surrounding the hybrid gold-polymer microparticles. The linear biopolymers may be chitosan, polyacrylic acid (PAA), PEG (methylether methacrylate), agarose, polyvinyl alcohol, hydroxypropyl cellulose, alginic acid, or other known polymer many of which are shown in FIGS. 3a-g. The variability of the polymers and synthetic conditions in FIGS. 1-3 are useful for the control of the Au NP properties and the versatility of their uses. The microgel spherical matrix of PNIPAM is more compact compared to linear polymer matrixes, giving rise to narrower absorption peaks suggesting more uniform particles compared to those formed in polymer-stabilized samples. On the other hand, each of the other biopolymers offers other advantages so as to make using it as a stabilizer of Au NPs worthwhile. For example, alginic acid is a natural biodegradable biopolymer available in varieties of alginates, which are extracted from sea weeds. Chitosan is an FDA-approved derivative produced by deacetylation of chitin, which is the structural element in the exoskeleton of crustaceans (crabs, shrimp, etc.) and cell walls of fungi. Poly(ethylene glycol) or PEG is produced by the interaction of ethylene oxide with water, ethylene glycol or ethylene glycol oligomers; it is used in a variety of products including laxatives, skin creams, cetomacrogol, and sexual lubricants, frequently combined with glycerin. Agarose (also known as agar) is a gelatinous substance derived from seaweed; nutrient agar is used throughout the world to provide a solid surface containing medium for the growth of bacteria and fungi. PAA is capable of absorbing many times its weight in water, and hence is used in disposable diapers. Hydroxypropyl cellulose (HPC) is a derivative of cellulose with both water solubility and organic solubility; it is used as a topical ophthalmic protectant and lubricant. Polyvinyl alcohol has excellent film forming, emulsifying, and adhesive properties; it is also resistant to oil, grease and solvent, and is odorless and nontoxic.

Images of absorption spectra in the UV/Vis/NIR regions for different hybrid gold-polymer microparticle samples prepared under different conditions are not shown. The production of hybrid gold-polymer microparticles is demonstrated through appearance of plasmon absorptions characterized by broad signals at wavelengths longer than 500 nm. The plasmonic absorptions in the visible region, typically between 500-600 nm, represent gold nanospheres. Variation in the plasmon absorption peaks gives rise to different visible colors for the solution containing the particles. A graph of the absorption spectra in the UV/Vis/NIR regions for different hybrid gold-polymer microparticle samples prepared under different conditions shows a peak at about 540 nms. A significant situation arises when the absorption is controlled to extend to the near-infrared (NIR) at wavelengths of about 700 nm and longer; such absorptions (representing large hybrid gold-polymer microparticles) are particularly important for drug delivery and cancer treatment.

In addition, the size of the hybrid gold-polymer microparticles was also confirmed through TEM and SEM images. A variety of Au NPs are obtained, varying from small nanospheres with different radii to large nanorods, nanoprism, as well as other large polyhedral and irregular shapes (FIG. 4). These large hybrid gold-polymer microparticles are NIR-absorbing species, which are particularly important for drug delivery and cancer treatment. Hybrid gold-polymer microparticles prepared from Au(THT)Cl and PNIPAM-aa gel by stirring at under ambient conditions were characterized by FE-SEM and TEM. The FE-SEM shows the spatial confinement of hybrid gold-polymer microparticles inside the gel.

Hybrid gold-polymer microparticles prepared from Au(THT)Cl and PNIPAM-allylamine gel by photolysis and were characterized by FE-SEM and TEM.

FIG. 4 are TEM images of NIR-absorbing large hybrid gold-polymer microparticles, including rods, prisms, and polyhedral, prepared from Au(THT)Cl, PNIPAM-allylamine gel, and NaCl by photolysis.

NIR-absorbing large hybrid gold-polymer microparticles prepared from Au(Me2S)Cl and PNIPAM-allylamine gel by photolysis and characterized by TEM.

NIR-absorbing large hybrid gold-polymer microparticles, including prism-shaped particles and σ-shaped particles, prepared from Au(Me2S)Cl and PNIPAM-allylamine gel by thermolysis and characterized by TEM.

NIR-absorbing toxin-free Au NPs made by thermolysis of Au(THT)Cl and Au(Me$_2$S)Cl in PNIPAM-NH$_2$ microgel were characterized. The calculation shown illustrates that the use of a broad-band NIR lamp (covering the entire absorption range indicated by the peak area) instead of a common diode laser (providing only monochromatic light at 800 nm indicated by the peak height) may provide greater intensity for photothermal therapy applications for Au NPs. In addition the instant invention provides for the synthesizing of gold nanorods with different aspect ratios, or to extend the absorption range further into the NIR so that the absorption will overlap with some particularly powerful NIR lasers (e.g., Nd/YAG, whose output is 1064 nm instead of less powerful diode lasers that emit at 800 nm) or broad-band emitting NIR lamps. These gold nanorods provide a mechanism to facilitate the drug delivery or cancer cell killing resulting from the heat generated by the NIR-absorbing hybrid gold-polymer microparticles embedded in the hydrogels upon their exposure to the laser.

The present invention may use a variety of Au(I) complex precursors. For example, Au(Me$_2$S)Cl may be used as a starting material with the Me$_2$S ligand removed after the formation of the hybrid gold-polymer microparticles by heating above its boiling point of 28° C. Au(CO)Cl may be used as a starting material with the CO ligand automatically removed after hybrid gold-polymer microparticles even under ambient conditions. Au(THT)Cl is the most common starting material for Au(I) complexes where the THT ligand is volatile and can be readily removed after hybrid gold-polymer microparticle formation by heating. Au(I) complexes as a general class can lead to formation of hybrid gold-polymer microparticles in biopolymers and hydrogels by following similar procedures illustrated in FIGS. 1-3.

Figures 5A, 5B:
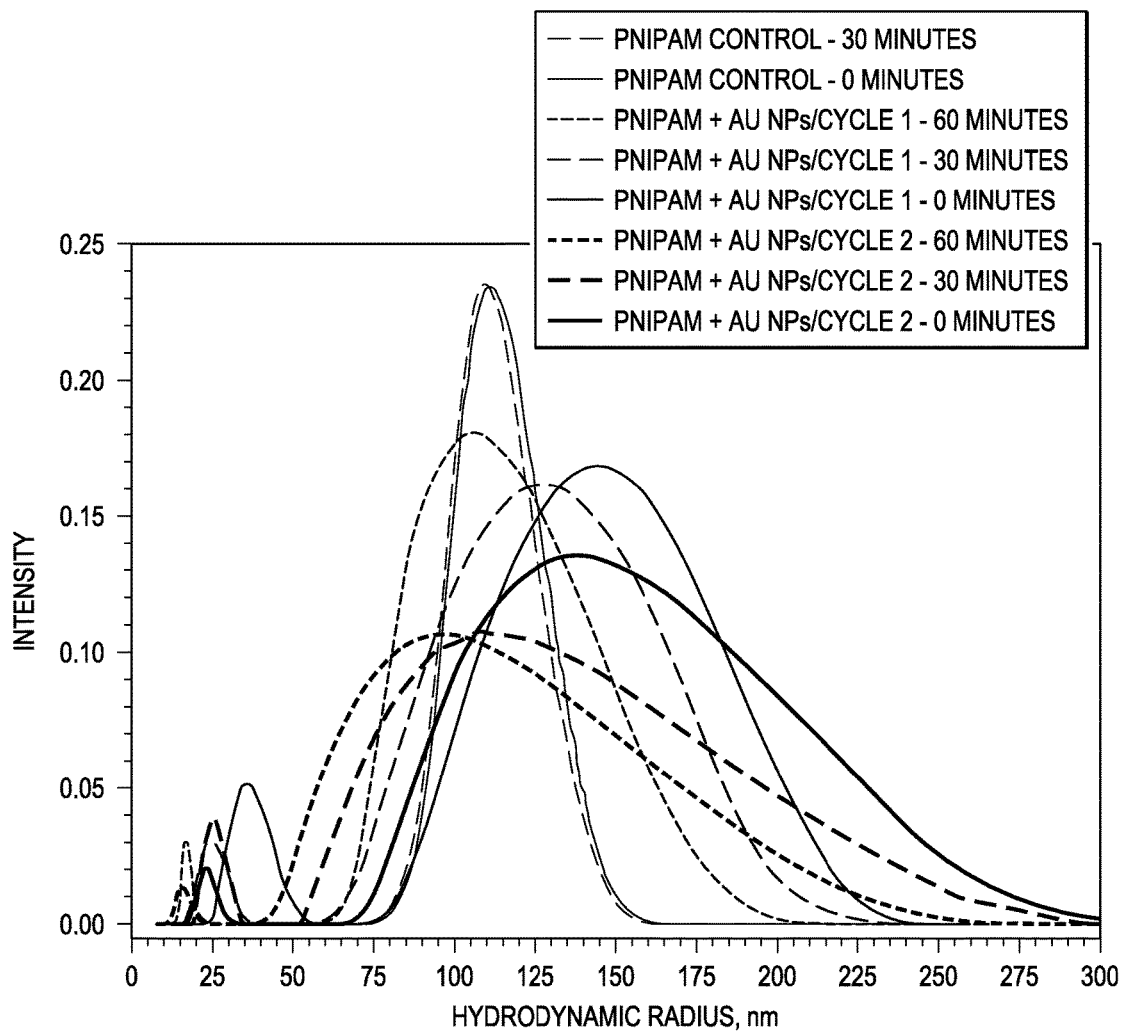
FIG. 5a is a spectrum and 5b is a table that demonstration of the usefulness of the non-toxic NIR-absorbing hybrid gold-polymer microparticles in this invention for photothermal therapy and drug delivery applications.
Figure 5E:
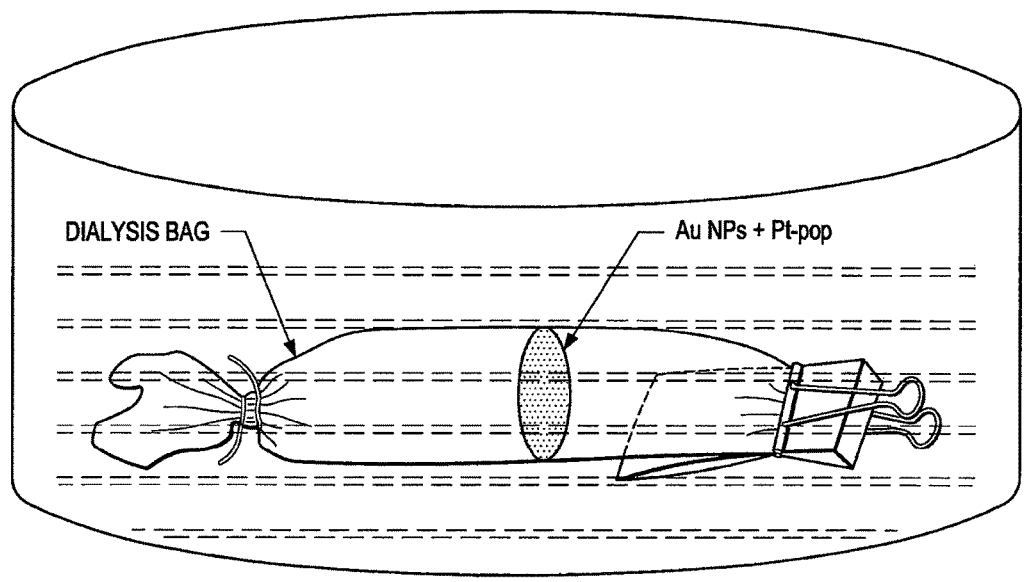
FIG. 5e is an image of the setup used in FIGS. 5a-5d.

The hybrid metal-polymer microparticles of the instant invention may be used in photothermal therapy and drug delivery. FIG. 5 demonstrates this potential. FIGS. 5a, 5c and 5d are graphs that demonstration of the usefulness of the non-toxic NIR-absorbing hybrid gold-polymer microparticles in this invention for photothermal therapy and drug delivery applications. FIG. 5b is a table that demonstration of the usefulness of the non-toxic NIR-absorbing hybrid gold-polymer microparticles in this invention for photothermal therapy and drug delivery applications. FIG. 22e is an image of the setup used in FIGS. 5a-5d. FIG. 5a shows the change in the hydrodynamic radius of nanocomposite PNIPAM microgels impregnated with NIR-absorbing Au NPs upon irradiation with an NIR lamp. The data is shown for two cycles of the PNIPAM/Au NP nanocomposite sample, as well as a control comprising PNIPAM alone without Au NPs. The sample shows rather significant de-swelling upon even more irradiation with a low-power NIR lamp, whereas the control does not show any significant de-swelling. The de-swelling indicates a temperature increase beyond the volume phase transition temperature of PNIPAM and therefore demonstrates the potential of photothermal therapy (using the heat generated, for example, to kill cancer cells upon conjugation to the Au NPs) and drug delivery (the de-swelling can lead to release of a drug molecule co-entrapped in the nanocomposite). FIG. 5b provides further validation of the drug delivery application showing the release of the tetrakis(μ-diphosphito)-diplatinate (II) (Pt-pop) drug molecule upon irradiation or thermal heating of PNIPAM gels impregnated with both Au NPs and this drug molecule.

In addition, the hybrid metal-polymer microparticles of the instant invention may be used as multifunctional contrast agents with both targeting and delivery moieties. For example, literature studies utilized toxic Au NPs to distinguish the presence of visible filapodia in natural tissue (*Nano Lett.* 2007, 7, 1338-1343); therefore, it will be more advantageous to perform such studies with the non-toxic Au NPs of this invention.

The hybrid metal-polymer microparticles of the instant invention that are small in size (absorb in the visible region) may be used for diagnosis of surface (e.g., skin) type cancer in place of small nanoparticles made by conventional synthesis methods. Such spherical gold or hybrid silver-polymer microparticles conjugated to antibodies specifically targeted to cancer cells have been used to detect single malignant cells by dark field microscopy and spectrophotometry, whereas photothermal therapy of surface (skin) cancers could be accomplished by use of the small spherical gold or hybrid silver-polymer microparticles by exposure to low energy visible continuous wave (CW) lasers whereas deeper penetration beyond skin requires NIR-absorbing larger nanoparticles and thus NIR irradiation sources (e.g., *Nano Lett.* 2005, 5, 829-834; *Cancer Lett.* 2006, 239, 129-135; *J. Am. Chem. Soc.* 2006, 128, 2115-2120; *Cancer Lett.* 2008, 269, 57-66; *Chem. Soc. Rev.* 2008, 37, 1896-1908). The lack of cytotoxicity and greater versatility of the hybrid metal-polymer microparticles stabilized in multiple biocompatible media in the instant invention render them a better replacement of the conventional more toxic nanoparticles for all these applications.

The present invention may use a variety of biopolymer and aqueous stabilizers. For example, the instant invention may use PNIPAM is a biocompatible polymer that can be derivatized with various functional groups; it represents the most extensively-studied stimulus-sensitive biopolymer nanoparticles as hydrogel materials in part due to phase change (swelling or contraction) in response to stimuli that changes the temperature in either direction of its lower critical solution temperature (LCST). The instant invention may also use Chitosan which is an FDA-approved biopolymer that is rather benign since it is derived from shrimp and other edible shellfish. Other biocompaticle polymers and aqueous stabilizers pertaining to this technology include PAA, PEG, PVA, agarose, alginic acid, HPC, and SDS; these are representative examples of such materials that were surveyed and tested but are not an exclusive list. In addition, a variety of functional groups on the PNIPAM microgels may be used. For example, varying the functional groups on PNIPAM gels from $NH_2$ to COOH or SH can improve the bio-conjugation ability of PNIPAM/Au NP hybrid nanocomposites.

Figure 6:
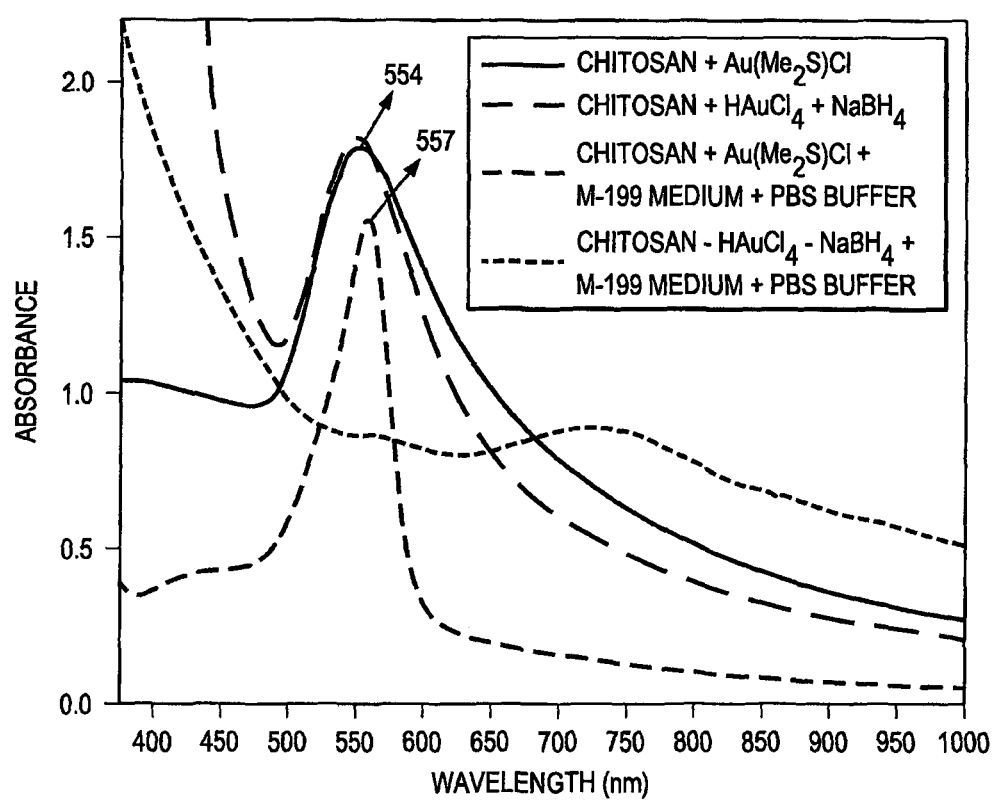
FIG. 6 demonstrates the stability of Au NPs prepared by the methods of this invention under physiological pH and temperature conditions (M-199 medium/PBS buffer) contrasted with the instability of particles prepared by the common methods.

The present invention allows greater stability and biocompatibility of Au NPs by the methods described herein compared to conventional synthesis methods. FIG. 6 illustrates this for chitosan-stabilized Au NPs synthesized by the method in this invention from $Au(Me_2S)Cl$ versus the conventional method from $HAuCl_4$ and $NaBH_4$. Upon adding the M-199 medium and PBS buffer to attain physiological conditions, the plasmon absorptions sharpened and the baseline decreased indicating sustained and actually enhanced stability of the Au NPs made following this invention. In contrast, the plasmon absorptions greatly broadened and the baseline increased for the Au NPs made following the conventional method, indicating their decreased stability and increased precipitation upon imposing physiological conditions.

Figure 7A:
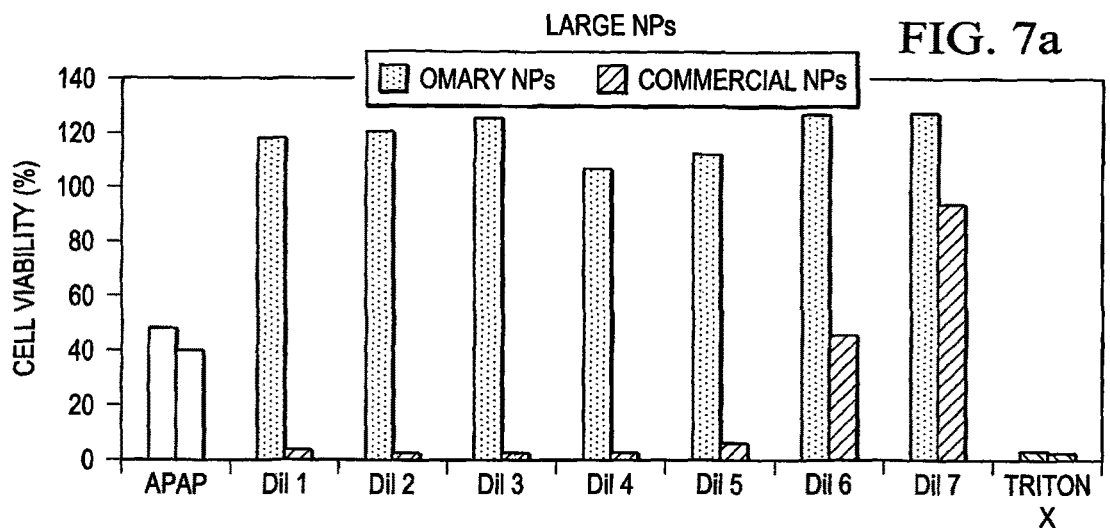
FIGS. 7a, 7b and 7c are graphs showing lack of toxicity of the Au NPs in this invention contrasted with extreme toxicity of commercial particles following conventional methods of syntheses.
Figure 7B:
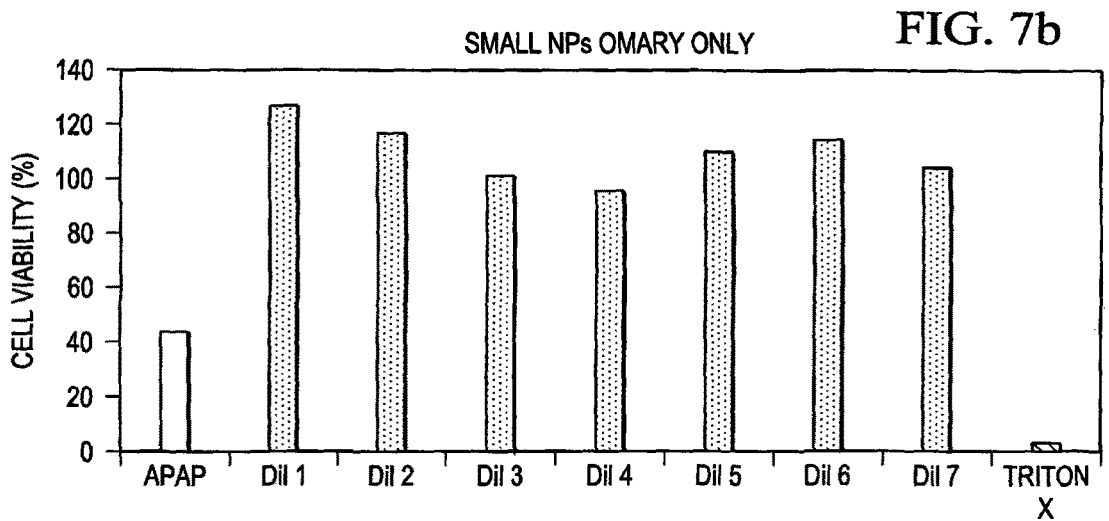

FIGS. 7a and 7b contrast the cytotoxicity (NCL assay method) of the Au NPs synthesized by the method in this invention with the cytotoxicity of CTAB-stabilized commercial Au nanorods. The commercial CTAB-stabilized samples killed essentially all cells (<5% viability up to dilution 4), similar to the TritonX control cell killer and significantly worse than the APAP acetaminophen control that shows ~40% viability. In contrast, the toxin-free Au NPs stabilized in FDA-approved chitosan made following this invention actually increased cell viability (promoted cell growth). Washing the commercial CTAB-stabilized Au NPs with biopolymers such as $PEG-NH_2$ to remove excess CTAB did not lead to significant reduction of their cytotoxicity, whereas no such workups are necessary for the non-toxic Au NPs made via this invention. The toxicity of the chemicals used in conventional methods of syntheses has been noted earlier in the literature as it has been found that the nanoparticles precursor $HAuCl_4$ and CTAB are toxic to cells at 10 nM concentrations (*Small* 2005, 1, 325-327).

Figure 7C:
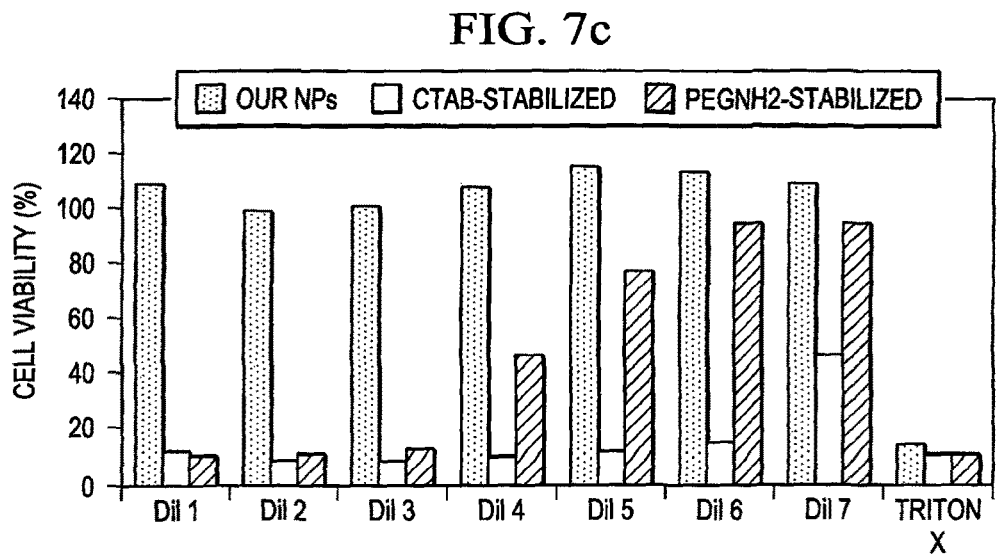

FIG. 7c is an image of a graph that contrasts the cytotoxicity of the photochemical synthesize non-toxic hybrid gold-polymer microparticles (Au NPs) from Au(I) precursors, including Au NPs capable of near-infrared (NIR) absorption. Although, the use of NIR-absorbing Au NPs in photothermal therapy (PTT) of cancer in animal models is known (e.g., El-Sayed et al., Cancer Letters 2008, 269, 57-66) the current art fails in human models to make benign particles because the known synthetic methods attain toxic particles due to the CTAB surfactant. In contrast, the cytotoxicity (NCL assay method) of the NIR-absorbing particles with the CTAB-stabilized commercial Au nanorods: The commercial samples (from Nanopartz), including those labeled "biocompatible" in which excess CTAB surfactant was washed with PEG-NH2 polymer, killed essentially all cells just like the TritonX control cell killer does. In contrast, our toxin-free particles stabilized in FDA-approved chitosan actually increased cell viability.

NIR absorbing hybrid gold-polymer microparticles as photothermal agents, generating enough heat for exhibiting phase transition temperature in hybrid environmental sensitive PNIPAM-co-allylamine hydrogel nanoparticles were characterized. Usage of a inexpensive NIR lamp, direct stabilization of NIR absorbing hybrid gold-polymer microparticles, insignificant variations in physico-chemical properties of hydrogel nanoparticles make these hybrid nanomaterials highly competitive compared to existing analogues popularized by Kumacheva et al works. ("Microgels Loaded with Gold Nanorods: Photothermally Triggered Volume Transitions under Physiological Conditions", Langmuir 2007, 23, 196-201).

FIGS. 8a-8d are images of nanoparticles. FIG. 8a is an image of nanocomposix Ag nanoparticles, FIG. 8b is an image of nanopartz Au nanoparticles, FIG. 8c is an image of UNT Au nanoparticles and FIG. 8d is an image of UNT Au nanoparticles.

Referring now to FIG. 8e, the Table compares the conventional methods to the methods of the present invention. The conventional methods include three steps in the preparation of nanoparticles to evaluate from environmental and biological applications perspective: first, a choice of solvent medium for syntheses, second a choice of environmentally benign reducing agent, and third a choice of non-toxic materials for stabilization (non-toxic stabilizers).

Figure 9A:
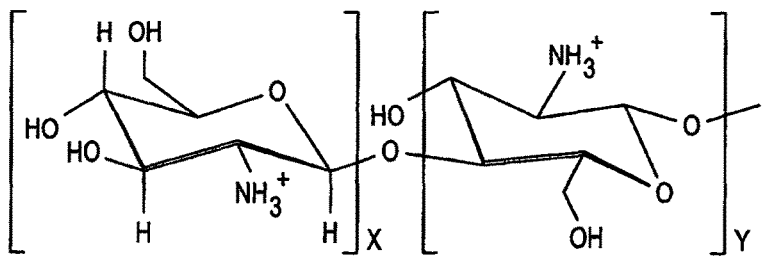
FIGS. 9a-9o are images of some of the one or more stabilizing agents included in the present invention.
Figure 9B:
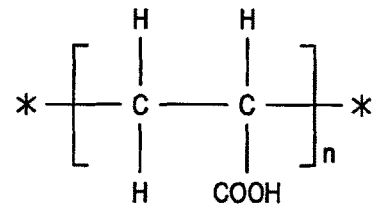
Figure 9C:
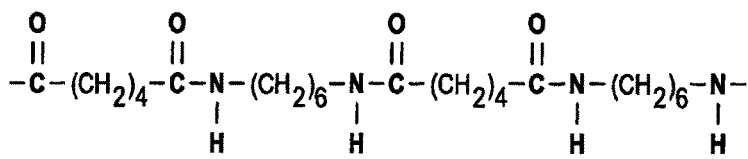
Figure 9D:
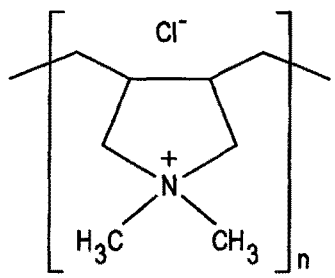
Figure 9E:
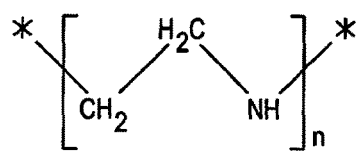
Figure 9F:
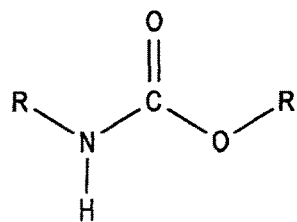
Figure 9G:
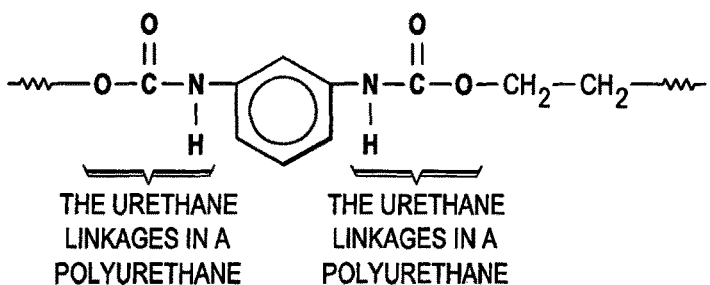
Figure 9H:
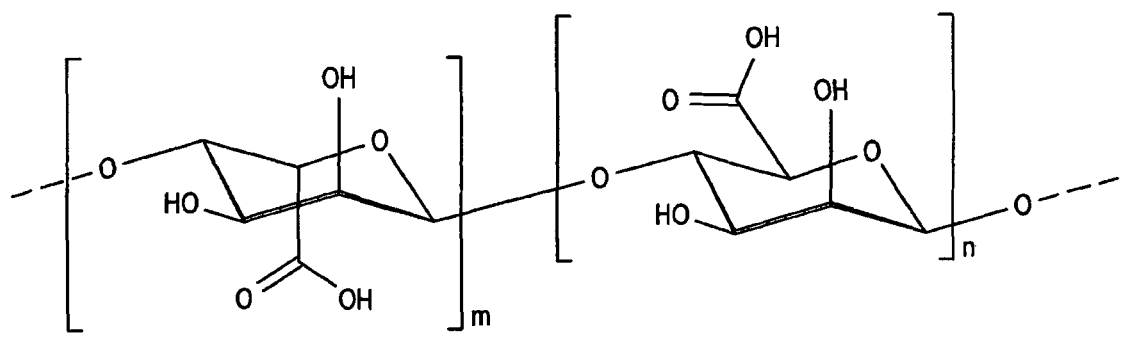
Figure 9I:
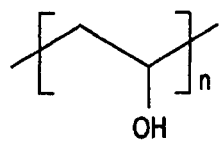
Figure 9J:
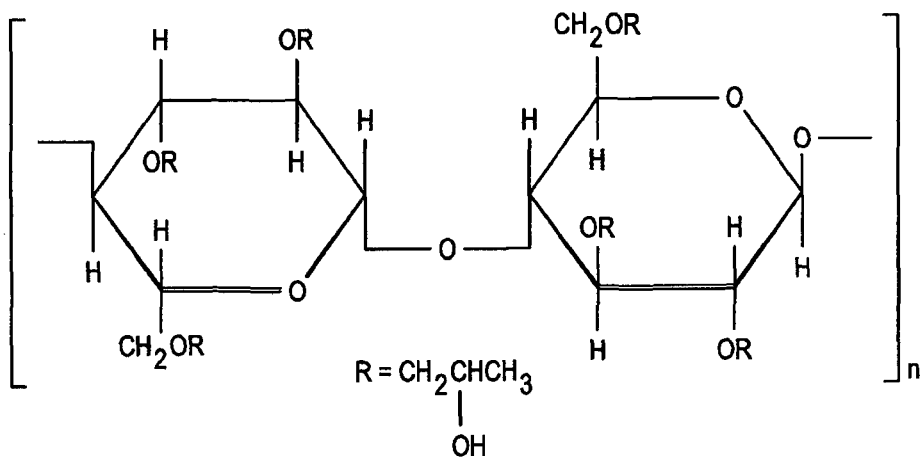
Figure 9K:
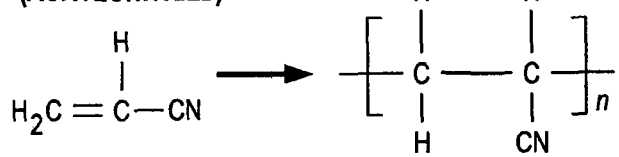
Figure 9L:
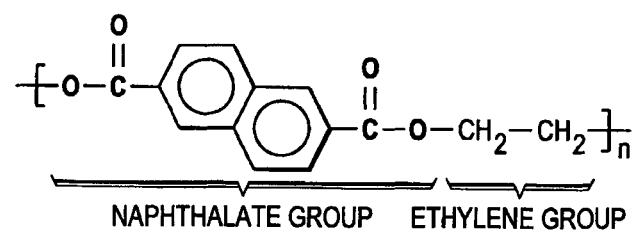
Figure 9M:
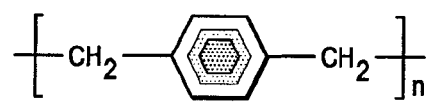
Figure 9N:
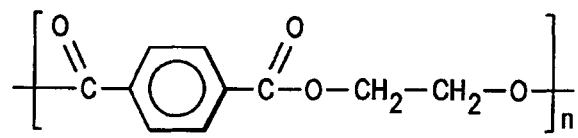
Figure 9O:
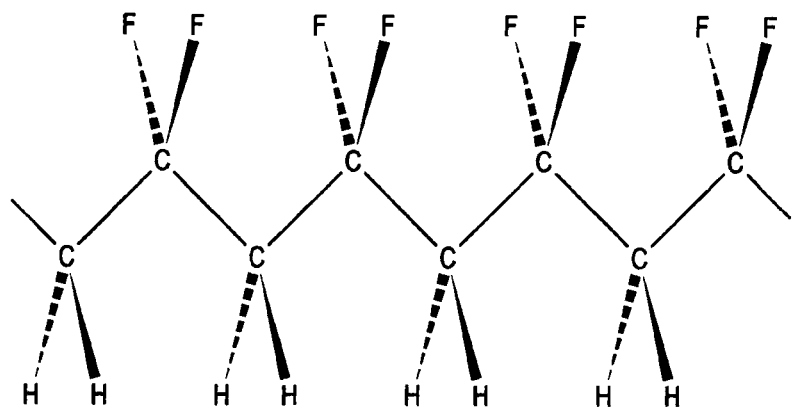

FIGS. 9a-9o are images of some of the one or more stabilizing agents included in the present invention. For example, the stabilizing agents may be chitosan (a), PAA (b), nylon (c), polydiallyl dimethyl ammonium chloride (d), polyethyleneimine (e), urethane (f), polyurethane (g), alginic acid (h), poly vinylacohol (i), hydroxyl propyl cellulose (j), polyacrylonitrile (k), poly(ethylenenapthalate) (l), Parylene (m), poly(ethylenetetrapthalate) (n), and poly(vinilydinefluoride) (o).

Figure 10:
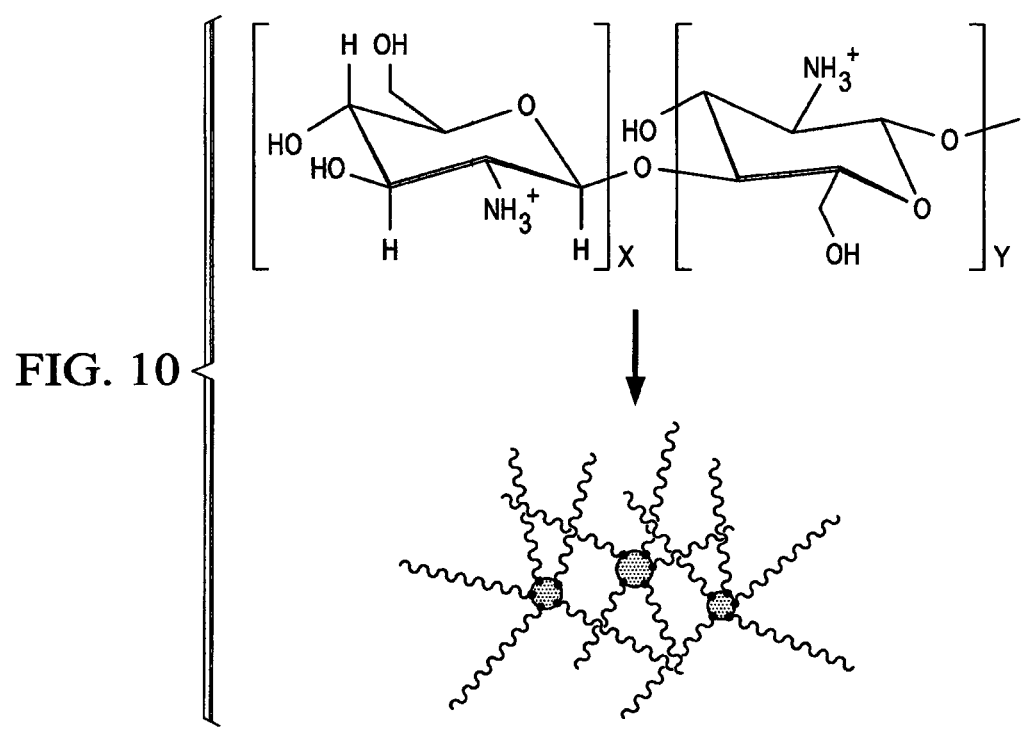
FIG. 10 is an image of the mechanism of formation and stabilization of AgNPs.

FIG. 10 is an image of the mechanism of formation and stabilization of AgNPs. Chitosan is combined with a silver salt and undergoes photochemistry to produce polymer stabilized spherical anisotropic hybrid silver-polymer microparticles. The polymer may be chitosan PVA, PAA, Alginic, nylon, polyurethane or polyacrylonitrile, etc.

Figure 11A:
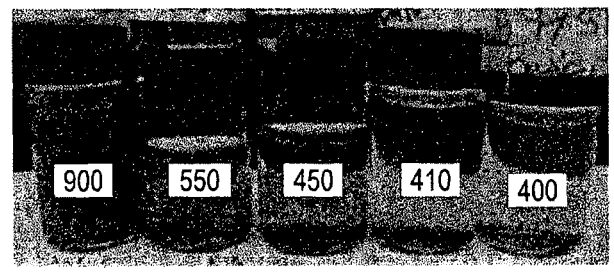
FIGS. 11a-11c are images of Ag NPs entrapped in different physical forms.
Figure 11B:
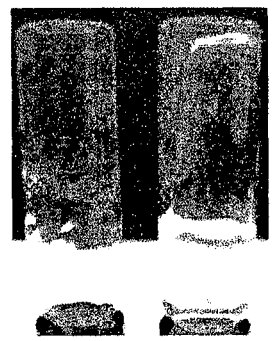
Figure 11C:

FIGS. 11a-11c are images of Ag NPs entrapped in different physical forms. FIG. 28a is an image illustrating the surface plasmon resonance (nm) with tenability through the spherical anisotropic AgNPs. FIG. 11b is an image illustrating the biocompatibility of gels with entrapped AgNPs. FIG. 11c is an image illustrating the nylon film, the initial nylon-AgNP film and the washed nylon-AgNP film.

Figure 12A:
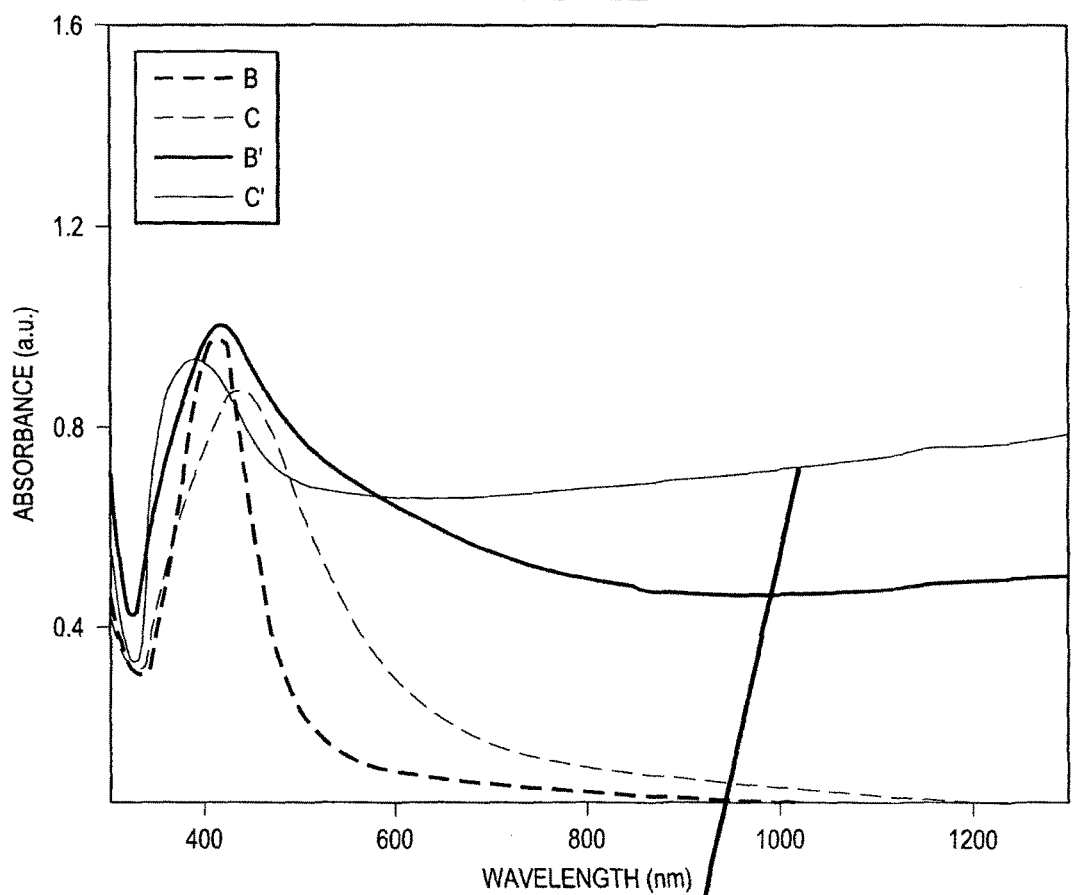
FIG. 12a is a graph of the absorbance versus wavelength demonstrating the significance of the glass material.
Figure 12C:
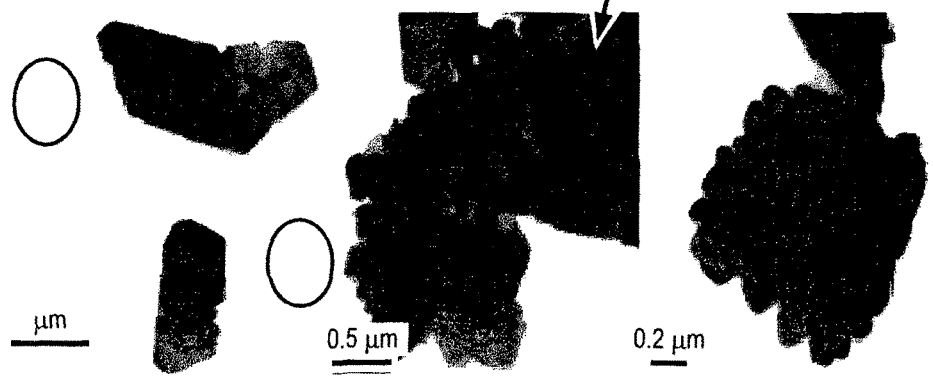
FIG. 12c is an image of the materials.
Figure 12B:
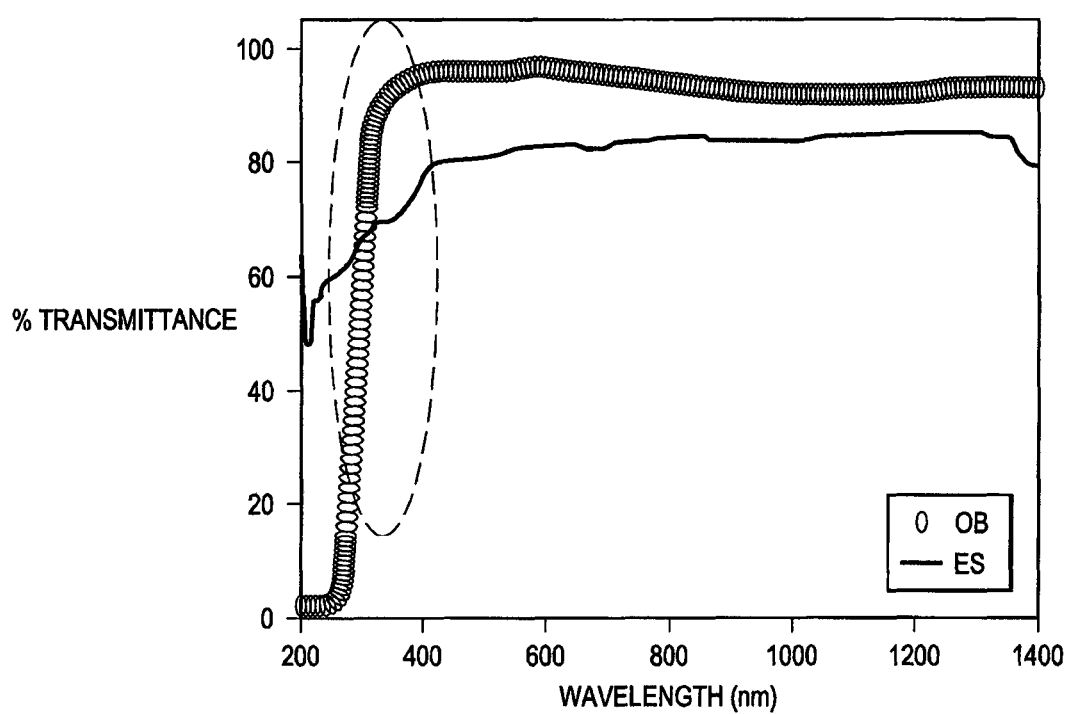
FIG. 12b is a graph of the transmission versus wavelength illustrating the OB orthoborosilicate and ES Quartz regions.

FIG. 12a is a graph of the absorbance versus wavelength demonstrating the significance of the glass material. FIG. 12b is a graph of the transmission versus wavelength illustrating the OB orthoborosilicate and ES Quartz regions. FIG. 12c is an image of the materials.

Figure 13A:
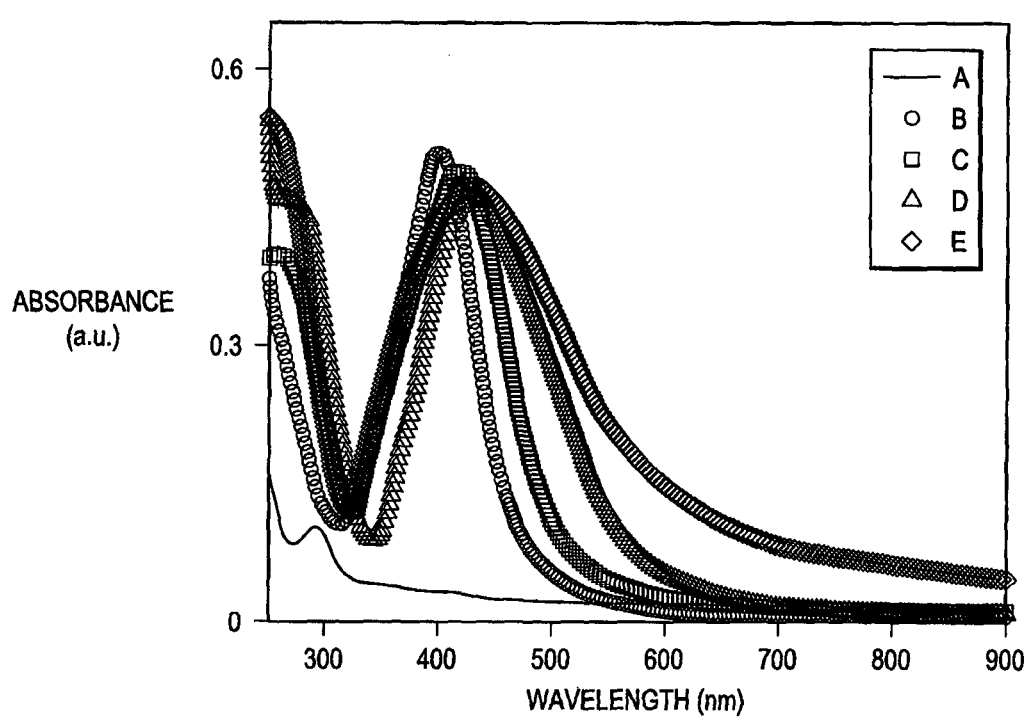
FIGS. 13a and 13b are graphs of the absorbance versus wavelength demonstrating the tenability and formation of spherical AgNPs in positively charged and negatively charged polymers respectfully.
Figure 13B:
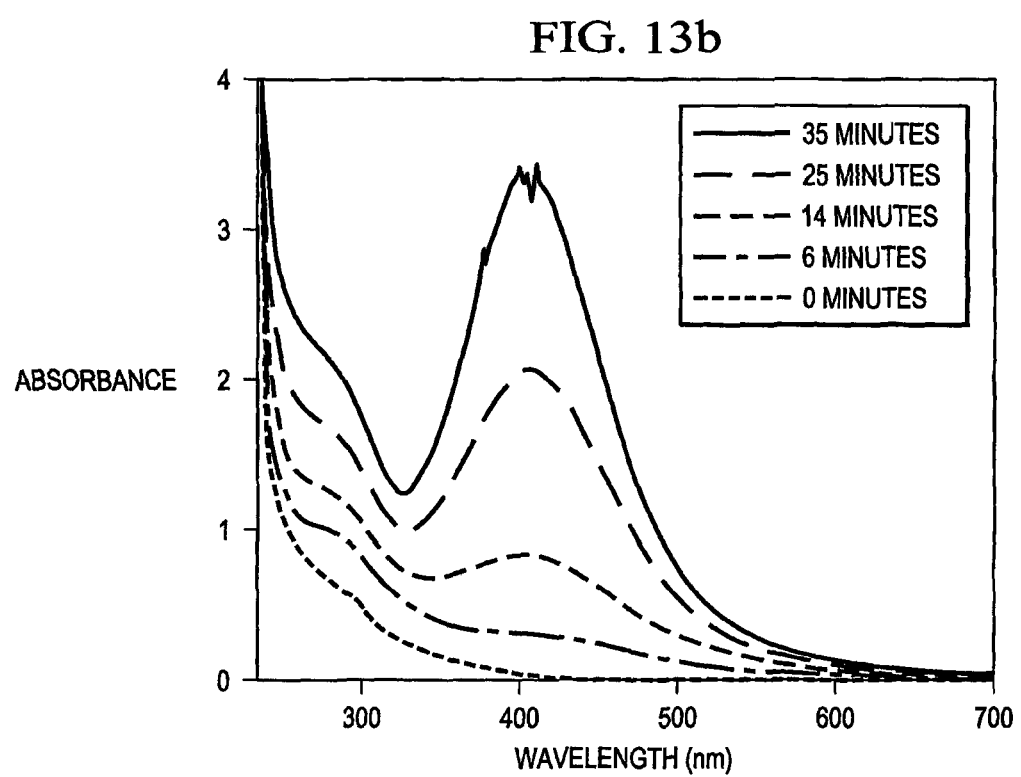

FIGS. 13a and 13b are graphs of the absorbance versus wavelength demonstrating the tenability and formation of spherical AgNPs in positively charged and negatively charged polymers respectfully. A: is silver nitrate/CS solution, B: is 0.5 wt %/2.5 mM AgNO$_3$; C: is 0.1 wt %/2.5 mM AgNO$_3$; D: is 0.5 wt %/10 mM AgNO$_3$; E: is 0.1 wt %/10 mM AgNO$_3$; and F: is 0.1 wt %/15 mM AgNO$_3$.

Figure 14A:
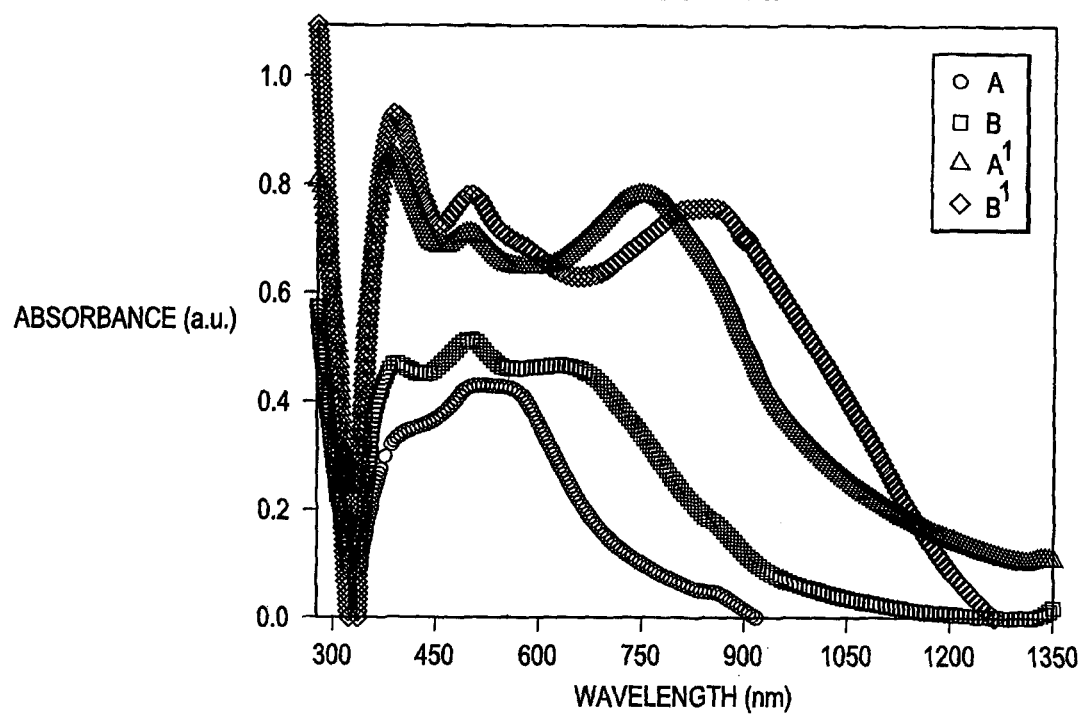
FIGS. 14a and 14b are graphs of the absorbance versus wavelength demonstrating the tenability and formation of spherical AgNPs via photochemistry and sunlight respectfully.
Figure 14B:
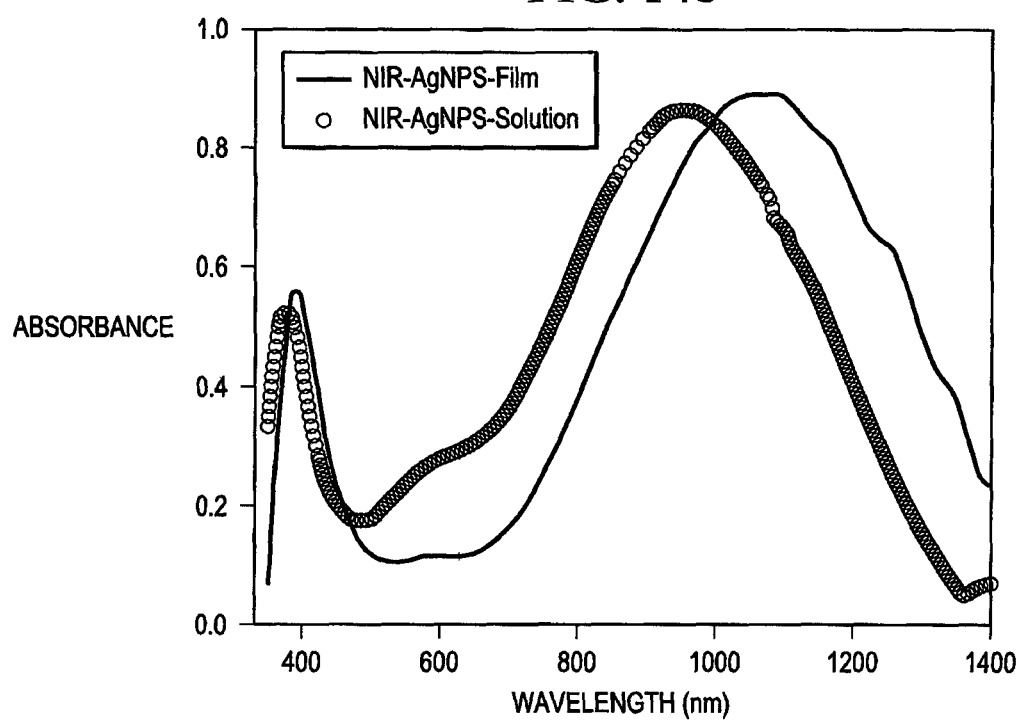

FIGS. 14a and 14b are graphs of the absorbance versus wavelength demonstrating the tenability and formation of spherical AgNPs via photochemistry and sunlight respectfully. A and B are 15-20 minute irradiations and A' and B' are 30-40 minute irradiations.

Figure 15A:
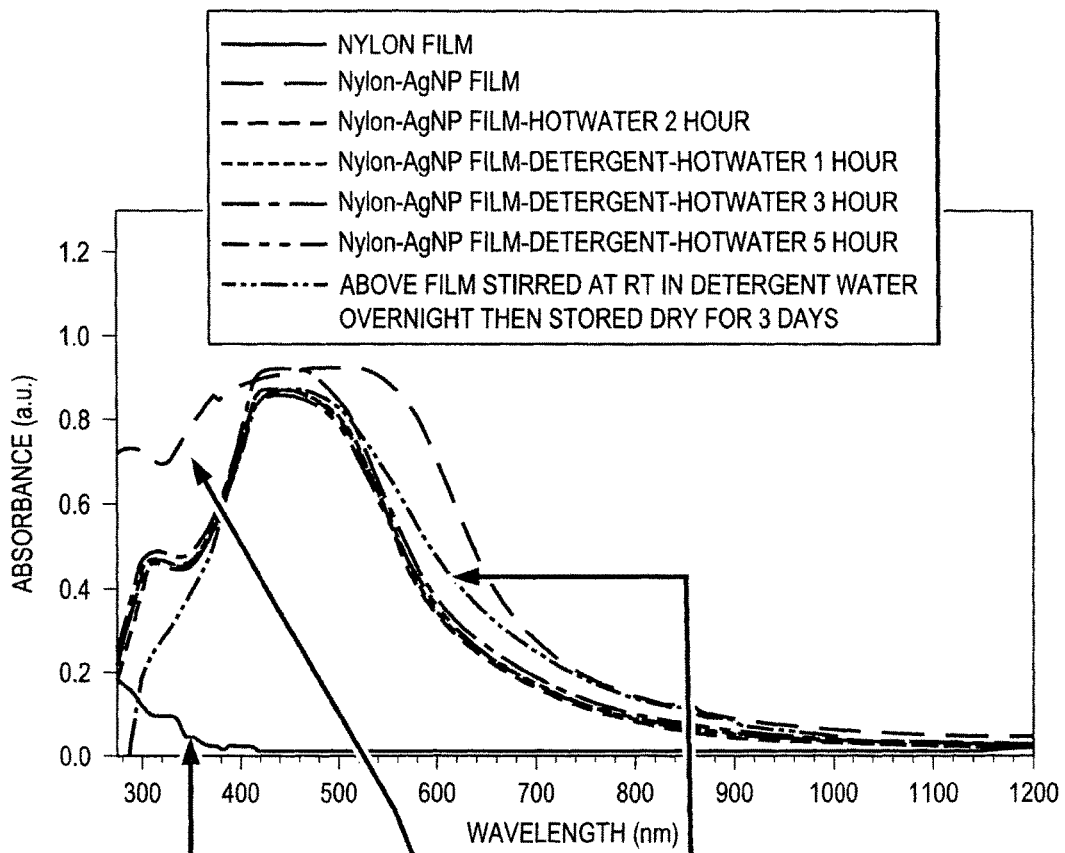
FIG. 15a is a graph of the absorbance versus wavelength demonstrating the formation of AgNPs within nylon polymer and water filtration using AgNPs nanofiber.
Figure 15B:
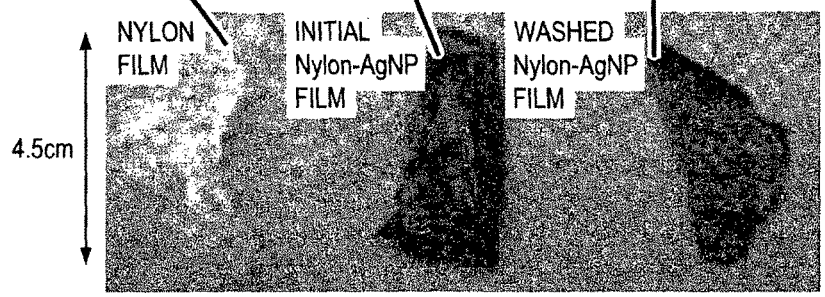
FIG. 15b is an image of the nylon film, initial nylon-AgNPs film, and washed nylon-AgNPs film.
Figure 15C:
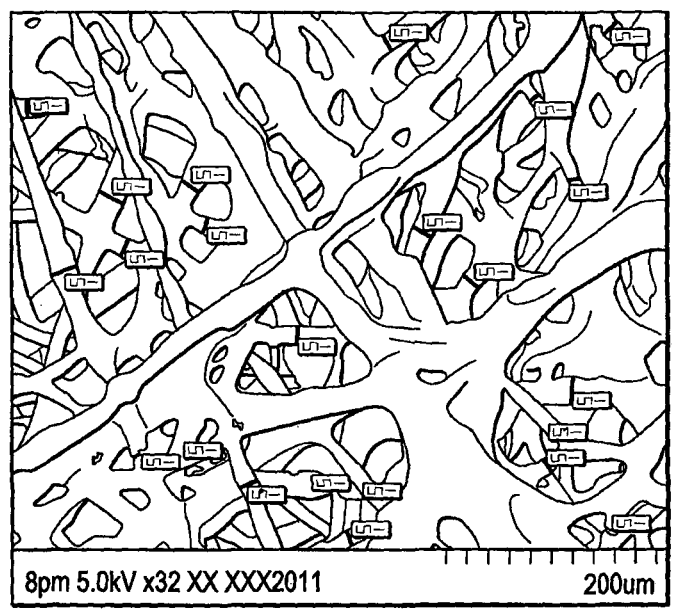
FIG. 15c is an image of the AgNP doped nanofiber.
Figure 15D:
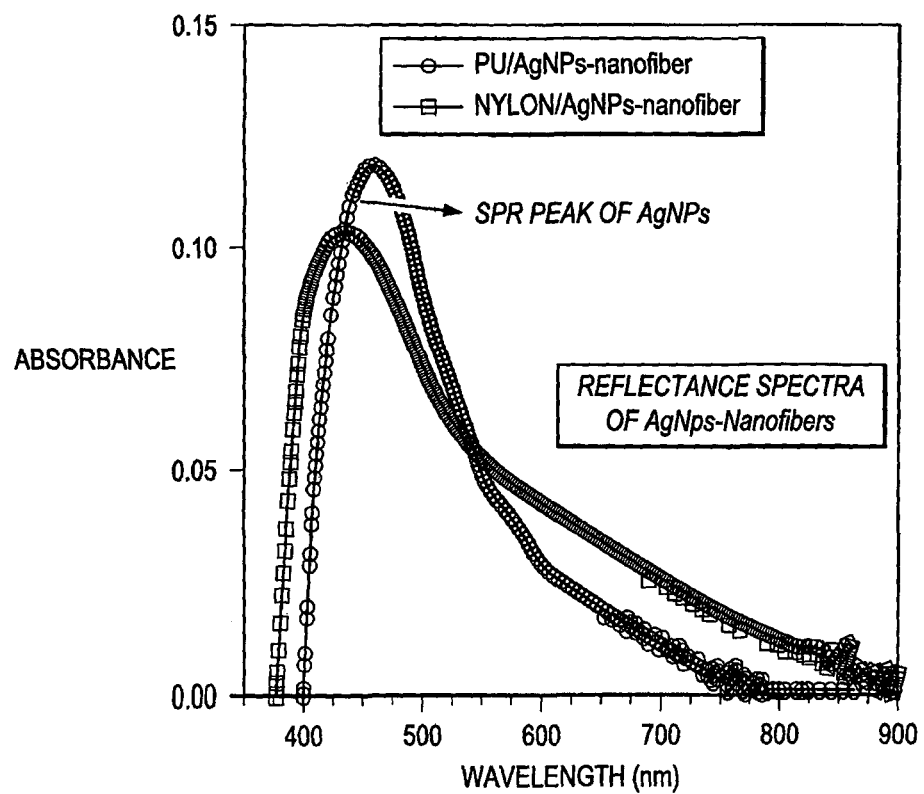
FIG. 15d is a graph of the absorbance versus wavelength demonstrating the reflectance spectrum of the AgNPs nanofiber.

FIG. 15a is a graph of the absorbance versus wavelength demonstrating the formation of AgNPs within nylon polymer and water filtration using AgNPs nanofiber. FIG. 15b is an image of the nylon film, initial nylon-AgNPs film, and washed nylon-AgNPs film. This demonstrates the stability of the AgNPs within the film even after hot water and detergent washings. FIG. 15c is an image of the AgNP doped nanofiber. FIG. 15d is a graph of the absorbance versus wavelength demonstrating the reflectance spectrum of the AgNPs nanofiber. 85% of the bacteria were killed in the AgNP doped nanofiber in water filtration studies.

Figure 16B:
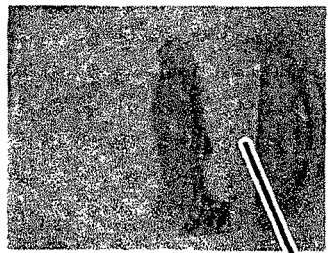
FIG. 16b is an image of the AgNP nylon film in hot water.
Figure 16C:
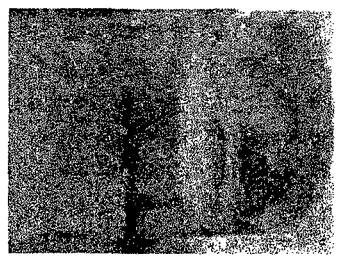
FIG. 16c is an image of the AgNP nylon film in hot detergent water.
Figure 16A:
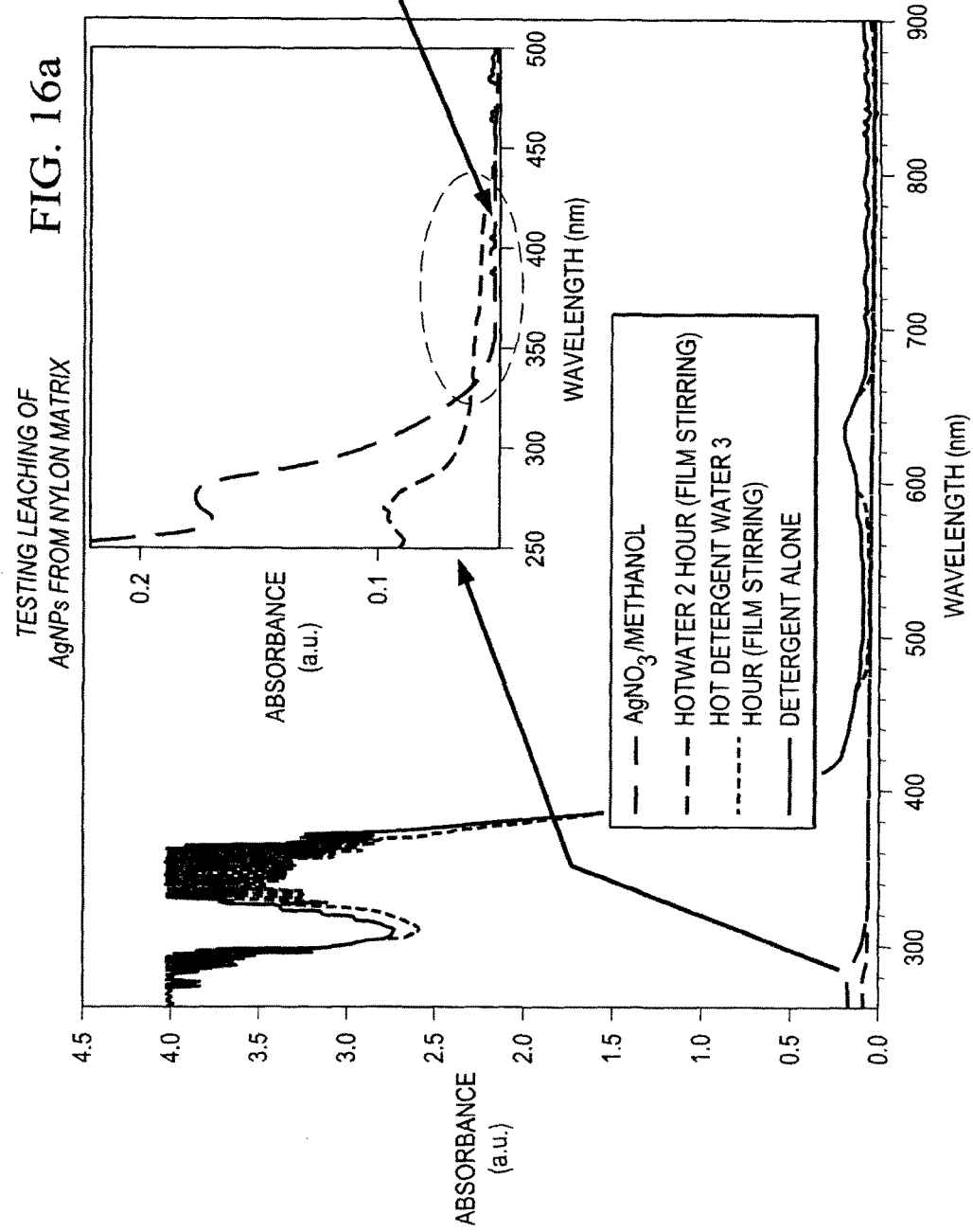
FIG. 16a is a graph of the absorbance versus wavelength demonstrating the leaching of AgNPs from nylon matrix.

FIG. 16a is a graph of the absorbance versus wavelength demonstrating the leaching of AgNPs from a nylon matrix, with the inset being a magnification of the graph at the lower wavelengths. FIG. 16b is an image of the AgNP nylon film in hot water. FIG. 16c is an image of the AgNP nylon film in hot detergent water. The weak adsorption from the hot water sample indicates a small degree of loss of some of the Ag ions or weak-adsorption of the AgNP during the initial stages.

Figure 17:
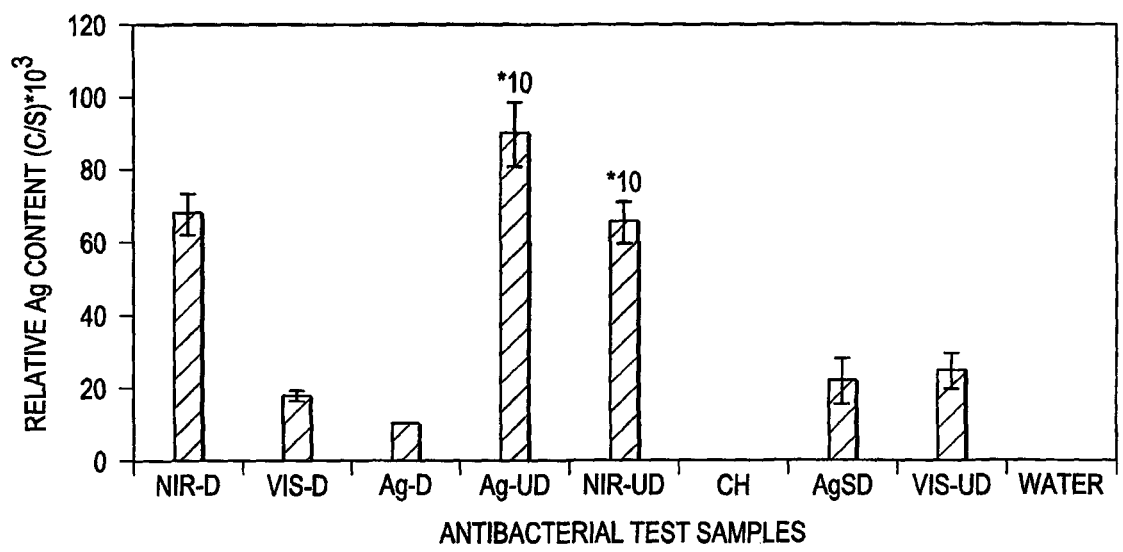
FIG. 17 is a plot of the antibacterial efficiency of AgNPs.

FIG. 17 is a plot of the antibacterial efficiency of AgNPs. The Ag-UD; Ag-D; and NIR-D had a Ag concentration of 20 mM. The VIS-UD; VIS-D; and AgSD exhibited an Ag concentration of 1 mM.

Figure 18:
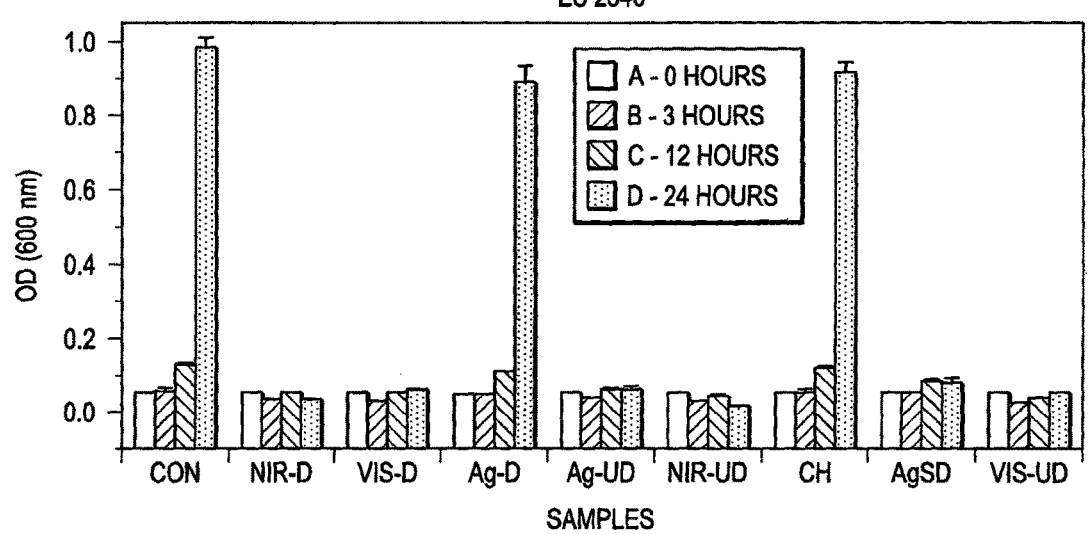
FIGS. 18, 19 and 20 are plots of the antibacterial efficiency of AgNPs against plant pathogenic bacteria *Pseudomonas syringae*.
Figure 19:
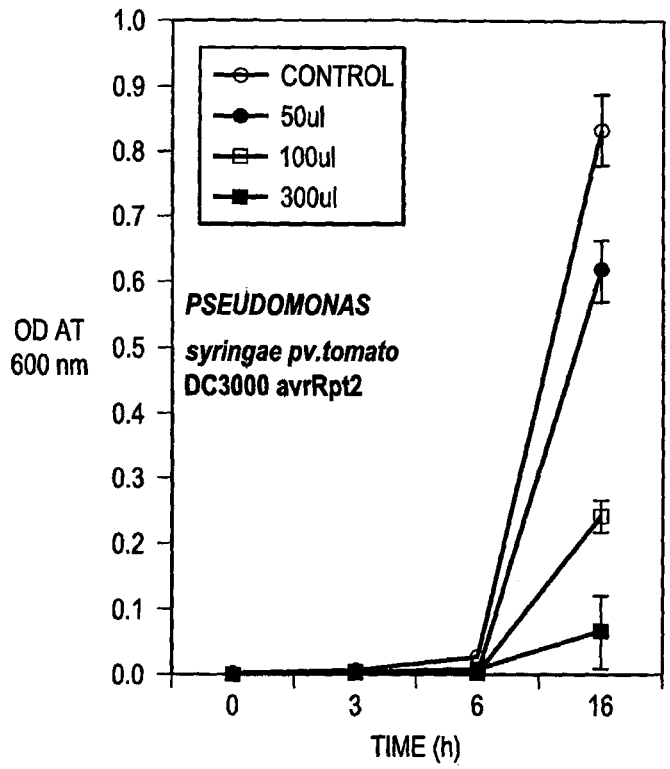
Figure 20:
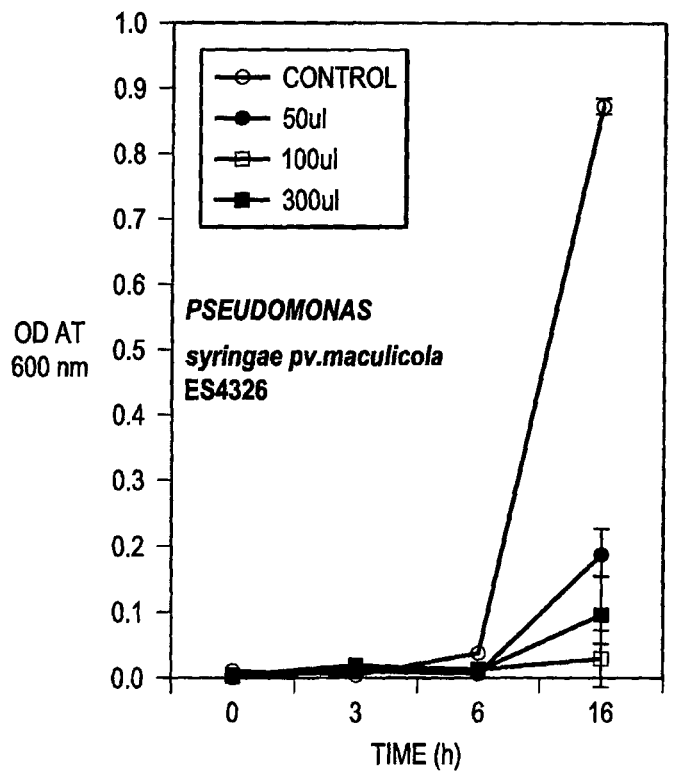
Figure 21:
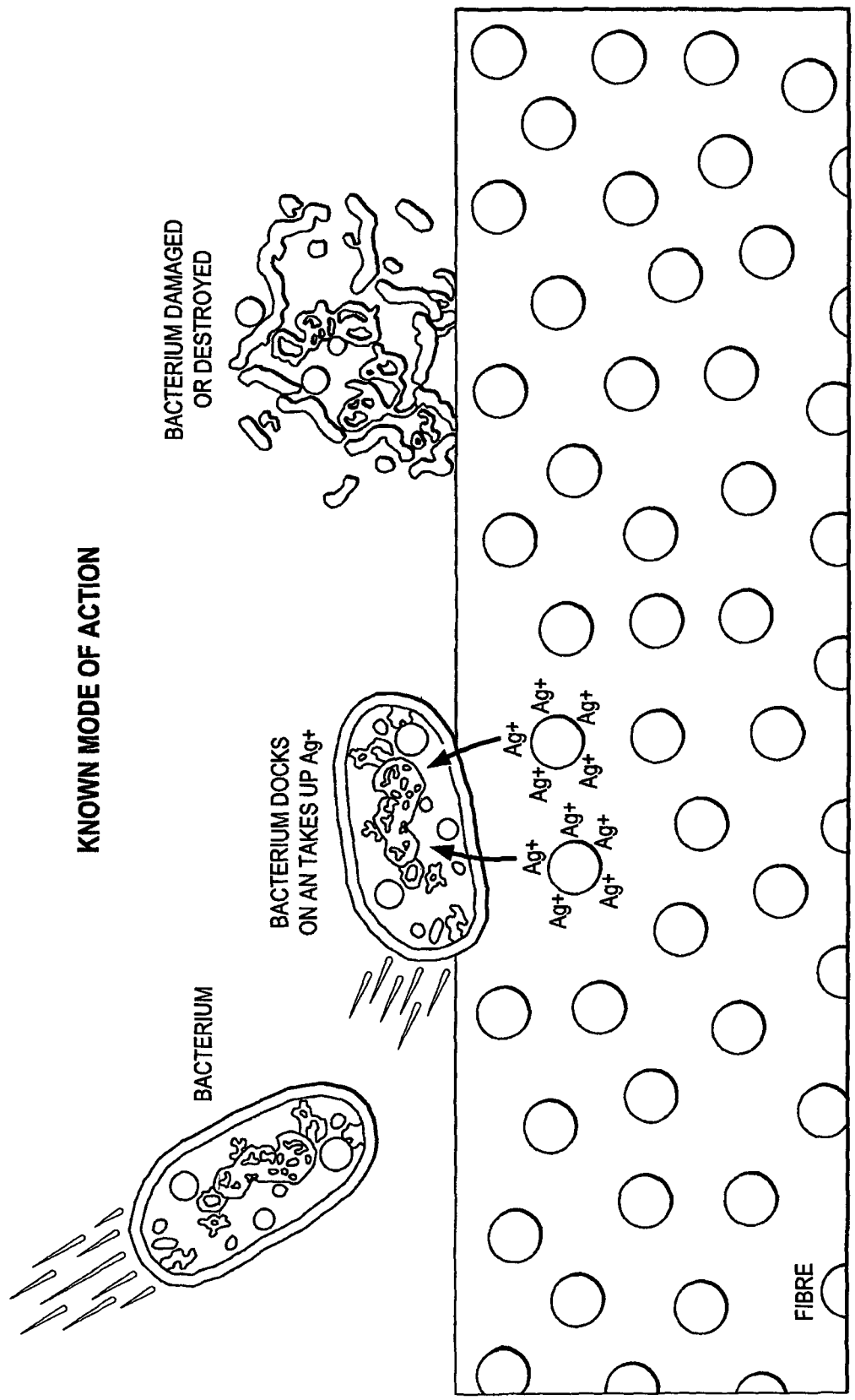
FIG. 21 is a schematic of one of the possible modes of action.

FIGS. 18, 19 and 20 are plots of the antibacterial efficiency of AgNPs against plant pathogenic bacteria *Pseudomonas syringae*. FIG. 21 is a schematic of one of the possible modes of action.

Furthermore, the instant invention may vary the reaction conditions such as pH, ionic strength, reaction time, irradiation time, and/or temperature fine-tunes the properties of the hybrid gold-polymer microparticles. One particularly important subset of the embodiments pertains to those at physiological conditions of pH, ionic strength and temperature to make the hybrid nanocomposites suitable vehicles. In addition, the instant invention provides a method of synthesis of hybrid gold-polymer microparticles in the absence of traces of reducing agents in biologically-compatible media and without by-products from the Au(I) precursors.

Size and shape variability to achieve strong plasmonic absorptions at wavelengths longer than about 700 nm to allow enhanced biological activities, e.g., photodynamic therapy, deep penetration of tissue, and heat-stimulated killing of tumors require such long absorption wavelengths for Au NP absorptions. Shorter-wavelength plasmonic absorptions of hybrid gold-polymer microparticles are still useful, particularly for skin cancer; see for example: El-Sayed et al., *Cancer Letters* 2006, 239, 129; *J. Am. Chem. Soc.* 2006, 128, 2115.

Chitosan-stabilized hybrid gold-polymer microparticles of the instant invention offer advantages for applications such as DNA delivery, heavy-metal sensing, medical diagnostics using films for surface-enhanced Raman spectroscopy (SERS), and other biological applications. All applications that utilize Chitosan-stabilized hybrid gold-polymer microparticles can be improved upon using our toxin-free Chitosan-stabilized hybrid gold-polymer microparticles instead of those known to the skilled artisan. For example, and each incorporated herein by reference: Hilborn, J. G.; Dutta, J.; Sugunan, A. "Heavy-Metal ion sensors using Chitosan-capped hybrid gold-polymer microparticles", *Science and Technology of Adv. Mat.* 2005, 6, 335: Use of Chitosan serves dual purpose of providing sufficient steric hindrance ensuring stability of the colloid and also to functionalize the nanoparticles for use as sensors. Applications of hybrid gold-polymer microparticles as sensors are usually based on detecting the shifts in surface plasmon resonance (SPR) peak, due to either change in the dielectric constant around the nanoparticles as a result of adsorption of analyte molecules, or due to analyte-induced agglomeration of the nanoparticles. Kim, Y. H.; Yi, K. H.; Bahadur, K. C.; Bhattarai, R. S. "Hydrophobically modified Chitosan/hybrid gold-polymer microparticles for DNA delivery", *J. Nanopart. Res.* 2008, 10, 151: Potentiality of Chitosan as a non-viral gene carrier has been extensively considered. In acidic pH the protonated amine groups of Chitosan can effectively bind to DNA and condense in to microparticles. Aroca, R. F.; Dos Santos, D. S.; Goulet, P. J. G.; Pieczonka, P. W.; Oliveira, N. O. "Hybrid gold-polymer microparticles embedded, self-sustained Chitosan films as substrates for surface enhanced raman scattering" *Langmuir* 2004, 20, 10273: Self sustained, biodegradable Chitosan films containing Au nanostructures fabricated for trace analysis using surface-enhanced Raman scattering. Yang, X.; Huang, H. "Chitosan mediated syntheses of hybrid gold-polymer microparticles multilayer", *Colloids and Surfaces. A: Physicochem. Eng. Aspects* 2003, 226, 77: Syntheses of Au NPs using modified Chitosan.

The instant invention provides PNIPAM microgel-loaded hybrid gold-polymer microparticles that are particularly useful for drug delivery and other applications due to their photothermally-triggered volume phase transition. All applications that utilize PNIPAM-stabilized hybrid gold-polymer microparticles can be improved upon using the toxin-free PNIPAM-stabilized hybrid gold-polymer microparticles of the instant invention instead of those known to the skilled artisan. For example, and each incorporated herein by reference: Kumacheva, E.; Fava, D.; Sanson, N.; Das, M. "Microgels loaded with gold nanorods: Photothermally triggered volume phase transition under physiological conditions", *Langmuir,* 2007, 23, 196. Lee, T. R.; Kim, J. H. "Hydrogel-Templated growth of large hybrid gold-polymer microparticles: Syntheses of thermally responsive hydrogel-Nanoparticle composites", *Langmuir,* 2007, 23, 6504. Long, X.; Tian, C.; Peng, Y.; Zheng, Z.; Deng, Z.; Zhao, X. "A kind of smart hybrid gold-polymer microparticles-hydrogel composite with tunable thermo-switchable electrical properties", *New J. Chem.* 2006, 30, 915. Willner, I.; Bourenko, T.; Shipway, N. A.; Gabai, R.; Yissar, V. P. "Hybrid gold-polymer microparticles/hydrogel composites with solvent-switchable electronic properties", *Adv. Mat.* 2001, 13, 1320. Shi, L.; Zhang, W.; Zheng, P.; Jiang, X. "Thermoresponsive hydrogel of Poly (glycidyl methacrylate-co-N-isopropylacrylamide) as a Nanoreactor of hybrid gold-polymer microparticles", *J. Poly. Sci. A: Poly. Chem.* 2007, 45, 2812. Lee, R. T; Kim, J. "Thermo- and pH-Responsive Hydrogel-coated Hybrid gold-polymer microparticles" *Chem. Mater.* 2004, 16, 3647. Long, X.; Peng, Y.; Deng, Z.; Ding, X.; Zhao, X. "Thermoswitchable Electronic Properties Of a hybrid gold-polymer microparticle/Hydrogel Composite", *Macromol. Rapid Commun.* 2005, 26, 1784. Cho, K.; Kim, Y. D; Cho, C. E. "Thermally responsive poly(N-isopropylacrylamide) monolayer on gold: syntheses, surface characterization, and protein interaction/adsorption studies", *Polymer* 2004, 45, 3195.

PEG polymer-stabilized hybrid gold-polymer microparticles of the instant invention are particularly useful due to the special biocompatibility of the polymer stemming from its biological inertness and the documented use for such hybrid systems in the treatment of rheumatoid arthritis in addition to other pharmaceutical applications. All applications that utilize PEG-stabilized hybrid gold-polymer microparticles can be improved upon using the toxin-free PEG-stabilized hybrid gold-polymer microparticles of the instant invention instead of those described in the literature. For example, and each incorporated herein by reference: Kataoka, K.; Nagasaki, Y.; Otsuka, H. "PEGylated nanoparticles for biological and pharmaceutical applications", *Adv. Drug Deliv. Reviews* 2003, 55, 403.

Agarose-stabilized hybrid gold-polymer microparticles of the instant invention are particularly useful because, being biologically benign, agarose ensures non-degradation of probe molecules and its gelation properties provide easy film formation for on-chip bio-sensing applications. All applications that utilize agarose-stabilized hybrid gold-polymer microparticles can be improved upon using the toxin-free agarose-stabilized hybrid gold-polymer microparticles of the instant invention instead of those described in the literature. For example, and each incorporated herein by reference: Guha, S.; Chandrasekhar, M.; Kattumuri, M. "Agarose-stabilized hybrid gold-polymer microparticles for surface enhanced Raman spectroscopic detection of DNA nucleosides", *Appl. Phys. Lett.* 2006, 88, 153114. Ozaki, Y.; Ai, K.; Lu, L. "Environmentally friendly syntheses of highly monodisperse biocompatible hybrid gold-polymer microparticles with urchin-like shape", *Langmuir* 2008, 1058. Au(Me$_2$S)Cl is available from Sigma-Aldrich. Au(CO)Cl is available from Strem. Au(THT)Cl is prepared using a previously described literature method (Usón, R.; Laguna, A. In *Organometallic Syntheses*; King, R. B., Eisch, J. J., Eds.; Elsevier: Amsterdam, 1986). In addition, the instant invention provides a method for using biologically benign polymers such as glucose, cellulose, starch, and polyacrylamide gels, thus offering a broader range of biologically benign stabilizers for the formation of hybrid gold-polymer microparticles.

BSA (Bovine Serum Albumin) known to be the most abundant protein in blood plasma and as a vehicle for intracellular transportation, BSA with great importance in pharmacology will be greatly beneficial with environmental sensitive hybrid gold-polymer microparticles attached. With significant improvement in biomedical applications for BSA stabilized hybrid gold-polymer microparticles, the current invention showed much easy and facile technique for stabilizing different size hybrid gold-polymer microparticles directly with in BSA contrasting with 2 to 3 step methods in literature. (*Phys. Chem. C* 2008, 112, 12282-12290). Like photochemical syntheses of BSA stabilized hybrid gold-polymer microparticles within PEG (polyethylene glycol) is synthesized in presence of a photoinitiator and AuCl$_4^-$ salt, which would leave presence of undesired by-products in the reaction While the descriptions above focused mostly on the synthesis and biomedical applications of hybrid gold-polymer microparticles synthesized from Au(I) complexes as precursors for the sake of illustration, the same methods can be applied for the synthesis of silver and copper nanoparticles from Ag(I) and Cu(I) precursors, as well as the synthesis of hybrid gold/silver, gold/copper, silver/copper, and gold/silver/copper complexes. FIG. 25 illustrates EDAX elemental analysis data for Au/Ag hybrid nanoparticles synthesized and characterized via similar methodologies to those discussed above. The chemistry and d-electronic count ($d^{10}$) of the three metals in their monovalent (+1) state make this generalization feasible.

The instant invention provides a method of making hybrid metal-polymer microparticles by converting a metal (I) precursor to a metal (0) and forming one or more hybrid metal-polymer microparticles from the metal (0) upon their controlled aggregation. The one or more hybrid metal-polymer microparticles are stabilized with one or more stabilizers to prevent agglomeration beyond the nanoscale. The metal (I) may be Au(THT)Cl, AuMe$_2$SCl, Au(CO)Cl or a plurality of Au(I) complexes with different ligands, as well as analogues thereof from Ag(I) and Cu(I) precursors. The step of converting may include photoreduction reaction, thermolysis reaction or both to convert the metal (I) to the metal (0). Stabilizers may include one or more polymers, one or more gels, one or more surfactants, agarose, hydrogels, PAA, PVA, Chitosan, PNIPAM, PNIPAM-aa, PNIPAM-allylamine, PAMAM, PEG, CTAB, BDAC or a combination thereof. In addition the present invention may be in contact with one or more hybrid metal-polymer microparticles to an active agent to form a site specific active agent delivery complex. The compositions of the instant invention may be used to conjugating the one or more hybrid metal-polymer microparticles to an active agent to form a site specific active agent delivery complex, to a binding agent for use as a diagnosis complex, used in surface enhanced Raman scattering for the detection of small molecules, or in conjugating the one or more hybrid metal-polymer microparticles to a cell surface for cell imaging. The metal (I) precursor may include a metal selected from the group consisting of gold (I), silver (I), and copper (I) complexes with different ligands and counter ions. The metal (0) includes at least one metal atom selected from the group consisting of gold, silver, and copper.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method of making a plasmonic hybrid metal-polymer microparticle complex comprising the steps of:
    forming a hybrid metal-polymer microparticle with a tunable near-infrared (NIR) plasmon absorption in an aqueous, biocompatible solution by
        providing an aqueous biocompatible solution;
        combining a metal (I) composition and one or more polymeric materials in the aqueous biocompatible solution;
        applying an electromagnetic radiation for 30-40 minutes, to the metal (I) composition to convert the metal (I) composition to a metal (0) composition;
        forming one or more hybrid metal-polymer microparticles from the metal (0);
        capping the one or more hybrid metal-polymer microparticles; and
    stabilizing the one or more hybrid metal-polymer microparticles with the one or more polymeric materials to prevent agglomeration and to provide the NIR plasmon absorption of the one or more hybrid metal-polymer microparticles between 700 nm-1200 nm; and
    forming one or more stabilized hybrid metal-polymer microparticles.

2. The method of claim 1, further comprising the step of adding one or more binding agents to the one or more hybrid metal-polymer microparticles to form a diagnosis complex that binds to a specific agent, wherein the one or more binding agents comprise one or more antibodies or oligonucleotides.

3. The method of claim 1, further comprising the step of adding one or more agents that enhance Raman scattering and identifying one or more small biological molecules using surface enhanced Raman scattering.

4. The method of claim 1, further comprising the step of adding an active agent and a pharmaceutical carrier to form a pharmaceutical plasmonic hybrid metal-polymer microparticle composition for delivery of an active agent.

5. The method of claim 1, wherein the metal (0) comprises at least one metal atom selected from the group consisting of aluminum, antimony, arsenic, barium, beryllium, bismuth, cadmium, calcium, cerium, chromium, cobalt, dysprosium, erbium, europium, gadolinium, gallium, hafnium, holmium, indium, iridium, iron, lanthanum, lead, lithium, lutetium, magnesium, manganese, mercury, molybdenum, neodymium, nickel, niobium, osmium, palladium, platinum, potassium, praseodymium, rhenium, rhodium, rubidium, ruthenium, samarium, scandium, strontium, tantalum, technetium, terbium, titanium, thallium, thorium, thulium, tin, tungsten, uranium, vanadium, ytterbium, yttrium, zinc, and zirconium.

6. The method of claim 1, wherein the metal (I) composition comprises a gold (I) complex, silver (I) complex or salt, copper (I) complex or salt, or combinations thereof.

7. The method of claim 1, wherein the metal (I) composition is made by adding a metal (I) precursor comprising Au(tetrahydrothiophene)Cl, $AuMe_2SCl$, Au(CO)Cl, $AgNO_3$ or $AgPF_6$ or $Cu(PPh_3)_3X$ complexes.

8. The method of claim 1, wherein the one or more polymer stabilizers comprise agarose, hydrogels, PAA (poly acrylic acid), PVA (poly vinyl alcohol), Chitosan, PNIPAM (Poly-N-isopropyl acrylamide), substituted PNIPAM, PAMAM (Polyamidoamine), PEG (Poly ethylene glycol), alginic acid, HPC (hydroxyl propyl cellulose), a crude phospholipid extract isolated from soybeans or a combination thereof.

9. The method of claim 1, wherein the one or more polymeric materials comprise Chitosan, Polyacrylic acid, Alginic acid, PEG, PVA, Agarose, albumin, bovine serum albumin (BSA), human albumin, synthetic albumin, HPC, PNIPAM, Nylon, polyurethane, polyacrylonitrile or a crude phospholipid extract isolated from soybeans.

10. A method of making a plasmonic hybrid metal-polymer microparticle complex comprising the steps of:
forming a hybrid metal-polymer microparticle with a tunable near-infrared (NIR) plasmon absorption in an aqueous, biocompatible solution by
providing an aqueous biocompatible solution;
combining a metal (I) composition wherein the metal (I) is silver and one or more polymeric materials in the aqueous biocompatible solution wherein one or more polymeric materials comprise Nylon, polyurethane, or polyacrylonitrile;
applying an electromagnetic radiation for 30-40 minutes to the metal (I) composition to convert the metal (I) composition to a metal (0) composition;
forming one or more hybrid metal-polymer microparticles from the metal (0);
capping the one or more hybrid metal-polymer microparticles; and
stabilizing the one or more hybrid metal-polymer microparticles with the one or more polymeric materials to prevent agglomeration and to provide the NIR plasmon absorption of the one or more hybrid metal-polymer microparticles between 700 nm-1200 nm; and
forming one or more stabilized hybrid metal-polymer microparticles.

11. The method of claim 1, wherein the hybrid metal-polymer microparticle composition is varied in size, shape or both.

12. The method of claim 1, further comprising the step adjusting one or more parameters selected from the group consisting of pH, ionic strength, temperature, centrifugation, reaction vessel material, optical filters, and combinations thereof, to adjust at least one of the tuning of the plasmon absorption energies or intensities and corresponding variation of at least one of size or shape of the one or more hybrid metal-polymer microparticles to adjust a plasmon absorption energy, an intensity or a combination thereof.

13. The method of claim 1, wherein the hybrid metal-polymer microparticle composition is varied in NIR plasmon absorption by varying a time of exposure and concentrations of the one or more polymeric materials and the metal (I) composition.

14. The method of claim 1, wherein the electromagnetic radiation is in the form of UV light, Sunlight, microwave radiation, far infrared radiation, near infrared radiation, visible radiation, x-rays, gamma rays, or high-energy gamma rays.

15. The method of claim 4, wherein the active agent is an agent that binds an antibody, a cell surface, or a small biological molecule.

16. The method of claim 4, wherein the active agent is delivered by a phase transition change in the pharmaceutical plasmonic hybrid metal-polymer microparticle composition; by a phase transition in the hybrid metal-polymer microparticle resulting from an electromagnetic change; or by a phase transition in the hybrid metal-polymer microparticle resulting from a thermal change.

17. A hybrid metal-polymer microparticle composite made by:
providing an aqueous biocompatible solution;
combining a metal (I) composition and one or more polymeric materials and one or more nanofibers;
applying an electromagnetic radiation for 30-40 minutes to the metal (I) composition;
converting the metal (I) composition to a metal (0) composition;
forming one or more hybrid metal-polymer microparticles from the metal (0);
capping the one or more hybrid metal-polymer microparticles;
stabilizing the one or more hybrid metal-polymer microparticles with the one or more polymeric materials to prevent agglomeration;
forming a hybrid metal-polymer microparticle composite; and
tuning of a near-infrared (NIR) plasmon absorption of the one or more hybrid metal-polymer microparticles between 700 nm-1200 nm by varying time of exposure, concentrations of the one or more polymeric materials, concentrations of the metal (I) composition or a combination thereof.

18. The hybrid metal-polymer microparticle composite of claim 17, wherein the metal (I) composition is silver to form an antipathogenic biocompatible polymer composition.

19. The hybrid metal-polymer microparticle composite of claim 17, wherein the one or more polymer stabilizers comprises agarose, hydrogels, PAA (poly acrylic acid), PVA (poly vinyl alcohol), Chitosan, PNIPAM (Poly-N-isopropyl acrylamide), substituted PNIPAM, PEG (Poly ethylene glycol), alginic acid, HPC (hydroxyl propyl cellulose), a crude phospholipid extract isolated from soybeans or a combination thereof.

20. The hybrid metal-polymer microparticle composite of claim 17, further comprising the step of forming the hybrid metal-polymer microparticle composite into a filter, a fiber, a cloth, a water filter, or a textile.

21. The method of claim 1, wherein the one or more polymeric materials comprise PNIPAM-aa (poly-N-isopropyl acrylamide-acrylic acid), PNIPAM-allylamine (Poly-N-isopropyl acrylamide-allylamine), or PNIPAM-SH.

22. The hybrid metal-polymer microparticle composite of claim 19, wherein the substituted PNIPAM comprises PNIPAM-aa (poly-N-isopropyl acrylamide-acrylic acid), PNIPAM-allylamine (Poly-N-isopropyl acrylamide-allylamine), or PNIPAM-SH.

\* \* \* \* \*